(12) United States Patent
Lardizabal et al.

(10) Patent No.: US 6,596,538 B1
(45) Date of Patent: Jul. 22, 2003

(54) FATTY ACYL-COA: FATTY ALCOHOL ACYLTRANSFERASES

(75) Inventors: Kathryn Dennis Lardizabal, Woodland, CA (US); James George Metz, Davis, CA (US); Michael W. Lassner, Davis, CA (US)

(73) Assignee: Calgene LLC, Davis, CA (US)

( * ) Notice: Subject to any disclaimer, the term of this patent is extended or adjusted under 35 U.S.C. 154(b) by 0 days.

(21) Appl. No.: 09/092,562

(22) Filed: Jun. 5, 1998

Related U.S. Application Data
(60) Provisional application No. 60/048,651, filed on Jun. 5, 1997.

(51) Int. Cl.⁷ .......................... C12N 15/32; C12N 5/04; C07H 21/04
(52) U.S. Cl. ...................... 435/419; 536/23.2; 536/23.6
(58) Field of Search ............................... 536/23.1, 23.2, 536/23.6; 435/69.1, 419, 468; 800/281

(56) References Cited

U.S. PATENT DOCUMENTS

| | | |
|---|---|---|
| 5,403,918 A | 4/1995 | Metz |
| 5,679,881 A | 10/1997 | Metz et al. |

FOREIGN PATENT DOCUMENTS

| | | |
|---|---|---|
| WO | WO 92/14816 | 9/1992 |
| WO | WO 93/10241 | 5/1993 |
| WO | WO 9310241 | 5/1993 |
| WO | WO 95/15387 | 6/1995 |
| WO | WO 9515387 | 6/1995 |
| WO | WO 95/33055 | 12/1995 |
| WO | WO 9855632 | 12/1998 |

OTHER PUBLICATIONS

Nakamura,, Y. et al., "Arabidopsis thaliana genomic DNA chromosome 5, P1 clone MTE17" EMBL Sequence Database, Jun. 19, 1998, XP002138250.
Lassner, et al., "A Jojoba B–Ketoacyl–CoA Synthase cDNA Complements the Canola Fatty Acid Elongation Mutation in Transgenic Plants" *The Plant Cell* vol. 8, 281–292 (1996).
Garver, et al., "A High–performance Liquid Chromatography–Based Radiometric Assay for Acyl–CoA: Alcohol Transacylase from Jojoba" *Analytical Biochemistry* vol. 207:335–340 (1992).
Shockey, et al., Photoaffinity Labeling of Developing Jojoba Seed Microsomal Membranes with a Photoreactive Analog of Acyl–Coenzyme A (Acyl–CoA) *Plant Physiol.* (1995) 107:155–160.
Wu, et al., "Studies of Biosynthesis of Waxes by Developing Jojoba Seed: III, Biosynthetis of Wax Esters from Acyl–CoA and Long Chain Alcohols" *Lipids*, vol. 16, No. 12:897–902 (1981).

Pollard, et al., "Studies on Biosynthesis of Waxes by Developing Jojoba Seed II. The Demonstration of wax Biosynthesis by Cell–Free Homogenates" *Lipids* vol. 14, No. 7:651–662 (1979).
Ohlrogge, et al., "Studies on Biosynthesis of Waxes on Developing Jojoba Seed Tissue" *Lipids*, vol. 13, No. 3:203–210 (1978).
Wildner, et al., Abstract: The Southwest Consortium Fifth Annual Meeting, Apr. 22–24, 1990 Las Cruces, New Mexico.
Pushnik, et al., Abstract: The Southwest Consortium Fourth Annual Meeting, Feb. 7, 1989.
Kamisaka, et al., "Characterization of the Diacylglycerol Acyltransferase Activity in the Lipid Body Fraction from an Oleaginous Fungus" *Journal of Biochemistry* vol. 116:1295–1301 (1994).
Abstract: National Plant Lipid Cooperative—*Plant Lipid Symposium* 1993, Minneapolis, Minnesota.
Kamisaka, et al., "Activation of Detergent–Solubilized Diacylglycerol Acyltransferase by Anionic Phospholipids" *Journal of Biochemistry* vol. 119:530–523 (1996).
Kamisaka, et al., "Purification and Characterization of Diacylglycerol Acyltransferase from the Lipid Body Fraction of an Oleaginous Fungus" *Journal of Biochemistry* vol. 121:1107–1114 (1997).
Kwanyuen, et al., "Subunit and amino acid composition of diacylglycerol acyltransferase from germinating soybean cotyledons" *Biochimica et Biophysica Acta* 1039:67–72 (1990).
Kwanyuen, et al., "Isolation and purification of diacylglycerol acyltransferase from germinating soybean cotyledons" *Biochimica et biophysica Acta* 877877:238–245 (1986).
Andersson, et al., "Purification of diacylglycerol: acyltransferase from rat liver to near homogeneity" *Journal of Lipid Research* vol. 35:535–545.
Kamisaka, et al., "Characterization of the Diacylglycerol Acyltransferase Activity in the Membrane Fraction from a Fungus" *Lipids* vol. 28, No. 7 583–587 (1993).
Polokoff, et al., "Solubilization, partial Purification and Characterization of rat liver microsomal diacylglycerol acyltransferase" *Biochimica et Biophysica Acta* 618:129–142 (1980).

*Primary Examiner*—Elizabeth F. McElwain
(74) *Attorney, Agent, or Firm*—Thomas P. McBride; Arnold & Porter

(57) ABSTRACT

By this invention, nucleic acid sequences encoding for fatty acyl-CoA: fatty alcohol acyltransferase (wax synthase) are provided, wherein said wax synthase is active in the formation of a wax ester from fatty alcohol and fatty acyl-CoA substrates. Of special interest is are nucleic acid sequences obtainable from a jojoba embryo wax synthase having an apparent molecular mass of approximately 33 kD. Also considered are amino acid and nucleic acid sequences obtainable from wax synthase proteins and the use of such sequences to provide transgenic host cells capable of producing wax esters.

15 Claims, 6 Drawing Sheets

DNA SEQUENCE OF THE PCR PRODUCT FROM PRIMERS
WSPEP14-F1 AND WSPEP33-R2

GATGACCCAWSNAAYGACCATGAGAAAAACAAGAGAACTCTGAGTTTTGAGTGGCGT
AAAGTTGTTCTTTTTGTTGCTAAGTTGGTGTTTTTGCGGTATTTAAAGATTTAT
GAGTTTAGAAAAGATTTGCCTCATTTTGTCCGGTGCTTTACTGTTTTCACTTC
TATCTCGGGACGGAGATCACCCCAGTTAGCAGCAAGCGCAGTCATAGCTCGAGCCACGCTA
GGGTTAGACCTATACCCCCAGTTCAACGAGCCCACCTCGCTGCAAGAC
TTCTGGGGGCGCAGGTGGAACCTCATGGTCTCAGACATCTTGGGTTGACAACATAC
CAGCCTGTCCGGCGTGTCCTCTCGAGGTGGGTCAGGCTCAGGGTCGCGCCGC
GCAATGTTGGTGGCGTTCACGGTGTCGGGCTAATGCATGAAGTGTTTTCTTNTAC
TTAACTCGCGCAGCCCGTGGGAGGTGACGGGGTTCTTTGTBTTGCATGGGGTT
TGCACAGCCCGTGGAGATGGTGGTGAAGAAGGCGGTTTCAGGCAAGGTGCGGCTGCGC
CGGGAGGTGTCAGGGCGCTCAGGGGGTGGGTTCGTGATGGTGACTGGAGGGTGGTTG
TTTTGCCGCAGCTGGTGAGGCATGGGGTAGATTTGAAGACCATTGATGAGTATCCT
GTCATGTTYAAYTAYACCCAGAAA

*FIG. 3A*

DNA SEQUENCE OF THE WAX cDNA INFRERED FROM 5' AND 3' RACE PRODUCTS.

```
GTCTCCATTACAATGGAGGTGGAGAAGGAGCTAAAGACCTTCTCAGAGGTATGGATC
TCCGCCATAGCCGCGCCGCCTCCTCCCCCGTCCCGCCCGTTGCCCCTCACGGC
GGCGCTCTCCGCCTCCTCCTCCTTCCACCTGTCGTCCTCCTCTTCATTTCCTCCCC
CTCCGCCCTCCTCCTCCTTCCACCTCGGCGCGGGCCCACCGCCTTGTATCTCGTCTGGCTT
GCCAACTTCAAGCTCCTTCTTCGCCTTTCATCTTGGCCCTTTATCTAACCCCTCT
CTCTCTCCTTCACTTCATCTGCTAAGTGAGAAAACAAGAGAACTCTGAGTTTTGAGTGGCGTAAAGTT
CCATCTAATGATCATGAGAAAAACAAGAGAACTCTGAGTTTTGAGTGGCGTAAAGTT
GTTCTTTTTGTTGCCCTCATTTTGTGATCTCGGTGCTTTACTGTTTTCACTTCTATCTC
AGAAAAGATTTGCCTCATTTTGTGATCTCGGTGCTTTACTGTTTTCACTTCTATCTC
GGGACGGAGATCACCCCAGTTCAACGAGCCATAGTGTCAGAGCTCGAACCTAGGGTTA
GACCTATACCCCAGTTGGAACCTCTCGAGGTGGGTCAGGCTCAGGTCGCGGCAATG
GGGCGCAGGTGGAACCTCTCGAGGTGGGTCAGGCTGTAATGCATGAAGTGTTTTCTTCTACTTAACT
GTCCGGCGTGTCCTCCTCAGGGTGTGGGGCTAATGCATGAAGTGTTTTCTTCTACTTAACT
TTGGTGGCGTTCACGGTGTCGGGGAGGTGACGGGAGGGCGGTTCGTGATGGTGACTGGTGACTCCTGTCATG
CGCGCGAGGCCCTCGTGGGAGGTGACGGGAGGGCGGTTCGTGATGGTGACTGGTGACTCCTGTCATG
GCCGTGGAGATGGTGGTGACGGGTGGGGTTCGTGATGGTGACTGGTGTCCTGTCATG
GTGTCAGGGCGCTGAGGCATGGGGGTAGATTTGAAGACCATTGATGATGAGAA
CCGCAGCTGGTGAGGCATGGGGGTAGATTTGAAGACCATTGATGATGAGAA
TTTAATTATACTCAGAAGAAATTGATGGGTTTGTTGGGTGTACGTCACGAGGAACCCAT
TGATGATCATGCAGATCACAGCAAGACAGGTCCGATTGTGGCATTTTGTGGTCACTTTTCA
GAAAATGCAGATCACAGCAAGACAGGTCCGATTGTGGCATTTTGTGGTCACTTTTCA
TTAAGTAGCCGGCCTGCCACCCTGTCCGATTGTTTTTAATGTTTTCTATGAATTTGAATAAT
TATCGTGTAGTATTTTGGTTTTTGTTTTTAATGTTTTCTATGAATTTGAATAAT
TTGTGCTTCATGAAAATTTTTTT
```

FIG. 3B

RADIOIMAGE OF TLC PLATE SHOWING INCORPORATION OF 1-$^{14}$C 16:0 CoA INTO WAX IN ASSAYS OF THE PELLET FRACTIONS PREPARED FROM DEVELOPING SEEDS OF ARABIDOPSIS TRANSFORMED WITH pCGN8559. A MEMBRANE FRACTION FROM DEVELOPING JOJOBA SEED IS THE POSITIVE CONTROL. BACKGROUND ACTIVITY IS ILLUSTRATED IN THE ASSAYS OF ARABIDOPSIS PLANTS 8612-3 AND 8613-2.

SEQUENCE LISTING

<160> NUMBER OF SEQ ID NOS: 25

<210> SEQ ID NO 1
<211> LENGTH: 651
<212> TYPE: DNA
<213> ORGANISM: Simmondsia chinensis
<220> FEATURE:
<221> NAME/KEY: unsure
<222> LOCATION: (1)..(651)
<223> OTHER INFORMATION: N represents either A, C, G or T

<400> SEQUENCE: 1

| | | | | | |
|---|---|---|---|---|---|
| gatgacccaw | snaaygacca | tgagaaaaac | aagagaactc | tgagttttga | gtggcgtaaa | 60 |
| gttgttcttt | ttgttgctaa | gttggtgttt | tttgcgggta | ttttaaagat | ttatgagttt | 120 |
| agaaaagatt | tgcctcattt | tgtgatctcg | gtgctttact | gttttcactt | ctatctcggg | 180 |
| acggagatca | ccttagcagc | aagcgcagtc | atagctcgag | ccacgctagg | gttagaccta | 240 |
| taccccagt | tcaacgagcc | atacttagcc | acctcgctgc | aagacttctg | ggggcgcagg | 300 |
| tggaacctca | tggtgtcaga | catcttgggg | ttgacaacat | accagcctgt | ccggcgtgtc | 360 |
| ctctcgaggt | gggtcaggct | gcggtgggag | gtcgccggcg | caatgttggt | ggcgttcacg | 420 |
| gtgtcgggc | taatgcatga | agtgttttc | ttntacttaa | ctcgcgcgag | gccctcgtgg | 480 |
| gaggtgacgg | ggttctttgt | bttgcatggg | gtttgcacag | ccgtggagat | ggtggtgaag | 540 |
| aaggcggttt | caggcaaggt | gcggctgcgc | tttttgccgc | agctggtgag | gcatgggta | 600 |
| gatttgaaga | ccattgatga | gtatcctgtc | atgttyaayt | ayacccagaa | a | 651 |

<210> SEQ ID NO 2
<211> LENGTH: 1334
<212> TYPE: DNA
<213> ORGANISM: Simmondsia chinensis

<400> SEQUENCE: 2

| | | | | | |
|---|---|---|---|---|---|
| gtctccatta | caatggaggt | ggagaaggag | ctaaagacct | tctcagaggt | atggatctcc | 60 |
| gccatagccg | ccgcctgcta | ctgccgcttc | gtccccgccg | ttgcccctca | cggcggcgct | 120 |
| ctccgcctcc | tcctcctcct | ccccgtcgtc | ctcctcttca | ttttcctccc | cctccgcctc | 180 |
| tcctccttcc | acctcggcgg | gcccaccgcc | ttgtatctcg | tctggcttgc | caacttcaag | 240 |
| ctccttctct | tcgcctttca | tcttggccct | ttatctaacc | cctctctctc | tctccttctc | 300 |
| ttcatctcca | ccaccctcct | ccccatcaag | ttcagagatg | acccatctaa | tgatcatgag | 360 |
| aaaaacaaga | gaactctgag | ttttgagtgg | cgtaaagttg | ttcttttgt | tgctaagttg | 420 |
| gtgttttttg | cgggtatttt | aaagatttat | gagtttagaa | aagatttgcc | tcattttgtg | 480 |
| atctcggtgc | tttactgttt | tcacttctat | ctcgggacgg | agatcacctt | agcagcaagc | 540 |
| gcagtcatag | ctcgagccac | gctagggtta | gacctatacc | cccagttcaa | cgagccatac | 600 |
| ttagccacct | cgctgcaaga | cttctggggg | cgcaggtgga | acctcatggt | gtcagacatc | 660 |
| ttggggttga | caacatacca | gcctgtccgg | cgtgtcctct | cgaggtgggt | caggctgcgg | 720 |
| tgggaggtcg | ccggcgcaat | gttggtggcg | ttcacggtgt | cggggctaat | gcatgaagtg | 780 |
| ttttcttct | acttaactcg | cgcgaggccc | tcgtgggagg | tgacggggtt | ctttgtgttg | 840 |
| catgggttt | gcacagccgt | ggagatggtg | gtgaagaagg | cggtttcagg | caaggtgcgg | 900 |
| ctgcgccggg | aggtgtcagg | ggcgctgacg | gtggggttcg | tgatggtgac | tggagggtgg | 960 |
| ttgttttgc | cgcagctggt | gaggcatggg | gtagatttga | agaccattga | tgagtatcct | 1020 |

```
gtcatgttta attatactca gaagaaattg atgggtttgt tggggtggtg atgaatgatg    1080
agatgatgat catgcatctt cttttcgga gatcggttgt acgtcacgag gagaacccat     1140
gaaaaatgca gatcaracgc aagacaggtc gggaaaaaaa aatgatcaat ttttccttaa    1200
gtagccggcc tgccaccctg tccgattgtg gcatttttgt ggtcactttt tcatatcgtg    1260
tagtattttt ggttttttgt tttaatgtt  ttctatgaat tttgaataat ttgtgcttca    1320
tgaaaatttt tttt                                                      1334
```

<210> SEQ ID NO 3
<211> LENGTH: 13
<212> TYPE: PRT
<213> ORGANISM: Simmondsia chinensis

<400> SEQUENCE: 3

Phe Val Pro Ala Val Ala Pro His Gly Gly Ala Leu Arg
 1               5                  10

<210> SEQ ID NO 4
<211> LENGTH: 14
<212> TYPE: PRT
<213> ORGANISM: Simmondsia chinensis

<400> SEQUENCE: 4

Thr Ile Asp Glu Tyr Pro Val Met Phe Asn Tyr Thr Gln Lys
 1               5                  10

<210> SEQ ID NO 5
<211> LENGTH: 13
<212> TYPE: PRT
<213> ORGANISM: Simmondsia chinensis

<400> SEQUENCE: 5

Phe Val Pro Ala Val Ala Pro His Gly Gly Ala Leu Arg
 1               5                  10

<210> SEQ ID NO 6
<211> LENGTH: 13
<212> TYPE: PRT
<213> ORGANISM: Simmondsia chinensis

<400> SEQUENCE: 6

Thr Ile Asp Glu Tyr Pro Val Met Phe Asn Tyr Thr Gln
 1               5                  10

<210> SEQ ID NO 7
<211> LENGTH: 9
<212> TYPE: PRT
<213> ORGANISM: Simmondsia chinensis

<400> SEQUENCE: 7

Phe Arg Asp Asp Pro Ser Asn Asp His
 1               5

<210> SEQ ID NO 8
<211> LENGTH: 17
<212> TYPE: DNA
<213> ORGANISM: Synthetic oligonucleotide
<220> FEATURE:
<221> NAME/KEY: unsure
<222> LOCATION: (1)..(17
<223> OTHER INFORMATION: N represents either A, C, G or T

```
<220> FEATURE:
<221> NAME/KEY: unsure
<222> LOCATION: (1)..(17)
<223> OTHER INFORMATION: Y represents either C or T

<400> SEQUENCE: 8
ttygtnccng cngtngc                                                17

<210> SEQ ID NO 9
<211> LENGTH: 17
<212> TYPE: DNA
<213> ORGANISM: Synthetic oligonucleotide
<220> FEATURE:
<221> NAME/KEY: unsure
<222> LOCATION: (1)..(17)
<223> OTHER INFORMATION: N represents either A, C, G or T
<220> FEATURE:
<221> NAME/KEY: unsure
<222> LOCATION: (1)..(17)
<223> OTHER INFORMATION: Y represents either C or T

<400> SEQUENCE: 9
gcnccncayg gnggngc                                                17

<210> SEQ ID NO 10
<211> LENGTH: 17
<212> TYPE: DNA
<213> ORGANISM: Synthetic oligonucleotide
<220> FEATURE:
<221> NAME/KEY: unsure
<222> LOCATION: (1)..(17)
<223> OTHER INFORMATION: N represents either A, C, G or T

<400> SEQUENCE: 10
gcnccnccrt gnggngc                                                17

<210> SEQ ID NO 11
<211> LENGTH: 17
<212> TYPE: DNA
<213> ORGANISM: synthetic construct
<220> FEATURE:
<221> NAME/KEY: unsure
<222> LOCATION: (1)..(17)
<223> OTHER INFORMATION: N represents either A, C, G or T

<400> SEQUENCE: 11
gcnacngcng gnacraa                                                17

<210> SEQ ID NO 12
<211> LENGTH: 20
<212> TYPE: DNA
<213> ORGANISM: Synthetic oligonucleotide
<220> FEATURE:
<221> NAME/KEY: unsure
<222> LOCATION: (1)..(17)
<223> OTHER INFORMATION: N represents either A, C, G or T
<220> FEATURE:
<221> NAME/KEY: unsure
<222> LOCATION: (1)..(17)
<223> OTHER INFORMATION: Y represents either C or T

<400> SEQUENCE: 12
acnathgayg artayccngt                                             20

<210> SEQ ID NO 13
<211> LENGTH: 20
<212> TYPE: DNA
<213> ORGANISM: Synthetic oligonucleotide
```

```
<220> FEATURE:
<221> NAME/KEY: unsure
<222> LOCATION: (1)..(17
<223> OTHER INFORMATION: N represents either A, C, G or T
<220> FEATURE:
<221> NAME/KEY: unsure
<222> LOCATION: (1)..(17
<223> OTHER INFORMATION: Y represents either C or T

<400> SEQUENCE: 13
ccngtnatgt tyaaytayac                                                   20

<210> SEQ ID NO 14
<211> LENGTH: 20
<212> TYPE: DNA
<213> ORGANISM: Synthetic oligonucleotide
<220> FEATURE:
<221> NAME/KEY: unsure
<222> LOCATION: (1)..(17
<223> OTHER INFORMATION: N represents either A, C, G or T
<220> FEATURE:
<221> NAME/KEY: unsure
<222> LOCATION: (1)..(17
<223> OTHER INFORMATION: Y represents either C or T

<400> SEQUENCE: 14
ttytgngtrt arttraacat                                                   20

<210> SEQ ID NO 15
<211> LENGTH: 20
<212> TYPE: DNA
<213> ORGANISM: Synthetic oligonucleotide
<220> FEATURE:
<221> NAME/KEY: unsure
<222> LOCATION: (1)..(17
<223> OTHER INFORMATION: Y represents either C or T

<400> SEQUENCE: 15
aacatbacbg grtaytcrtc                                                   20

<210> SEQ ID NO 16
<211> LENGTH: 20
<212> TYPE: DNA
<213> ORGANISM: Synthetic oligonucleotide
<220> FEATURE:
<221> NAME/KEY: unsure
<222> LOCATION: (1)..(17
<223> OTHER INFORMATION: N represents either A, C, G or T
<220> FEATURE:
<221> NAME/KEY: unsure
<222> LOCATION: (1)..(17
<223> OTHER INFORMATION: Y represents either C or T

<400> SEQUENCE: 16
gaygayccnw snaaygayca                                                   20

<210> SEQ ID NO 17
<211> LENGTH: 20
<212> TYPE: DNA
<213> ORGANISM: Synthetic oligonucleotide
<220> FEATURE:
<221> NAME/KEY: unsure
<222> LOCATION: (1)..(17
<223> OTHER INFORMATION: N represents either A, C, G or T

<400> SEQUENCE: 17
tgrtcrttns wnggrtcrtc                                                   20
```

```
<210> SEQ ID NO 18
<211> LENGTH: 29
<212> TYPE: DNA
<213> ORGANISM: Simmondsia chinensis

<400> SEQUENCE: 18
gatttgcctc attttgtgat ctcggtgct                              29

<210> SEQ ID NO 19
<211> LENGTH: 31
<212> TYPE: DNA
<213> ORGANISM: Simmondsia chinensis

<400> SEQUENCE: 19
gacctatacc cccaagttca acgagccata c                           31

<210> SEQ ID NO 20
<211> LENGTH: 30
<212> TYPE: DNA
<213> ORGANISM: Simmondsia chinensis

<400> SEQUENCE: 20
ttcaacgagc catacttagc cacctcgctg                             30

<210> SEQ ID NO 21
<211> LENGTH: 30
<212> TYPE: DNA
<213> ORGANISM: Simmondsia chinensis

<400> SEQUENCE: 21
aacaaccacc ctccagtcac catcacgaac                             30

<210> SEQ ID NO 22
<211> LENGTH: 30
<212> TYPE: DNA
<213> ORGANISM: Simmondsia chinensis

<400> SEQUENCE: 22
ttgcctgaaa ccgccttctt caccaccatc                             30

<210> SEQ ID NO 23
<211> LENGTH: 30
<212> TYPE: DNA
<213> ORGANISM: Simmondsia chinensis

<400> SEQUENCE: 23
aagatgtctg acaccatgag gttccacctg                             30

<210> SEQ ID NO 24
<211> LENGTH: 39
<212> TYPE: DNA
<213> ORGANISM: Synthetic oligonucleotide

<400> SEQUENCE: 24
ggatccgtcg acacaatgga ggtggagaag gagctaaag                   39

<210> SEQ ID NO 25
<211> LENGTH: 33
<212> TYPE: DNA
<213> ORGANISM: Synthetic oligonucleotide

<400> SEQUENCE: 25
gcatgcagat ctcaccaccc caacaaaccc atc                         33
```

FATTY ACYL-COA: FATTY ALCOHOL ACYLTRANSFERASES

This application claims priority to provisional application 60/048,651, filed Jun. 5, 1997.

TECHNICAL FIELD

The present invention is directed to enzymes, methods to purify, and obtain such enzymes, amino acid and nucleic acid sequences related thereto, and methods of use for such compositions in genetic engineering applications.

BACKGROUND

Through the development of plant genetic engineering techniques, it is possible to transform and regenerate a variety of plant species to provide plants which have novel and desirable characteristics. One area of interest for such plant genetic engineering techniques is the production of valuable products in plant tissues. Such applications require the use of various DNA constructs and nucleic acid sequences for use in transformation events to generate plants which produce the desired product. For example, plant functional promoters are required for appropriate expression of gene sequences, such expression being either in the whole plant or in selected plant tissues. In addition, selective marker sequences are often used to identify the transformed plant material. Such plant promoters and selectable markers provide valuable tools which are useful in obtaining the novel plants.

A desirable goal which involves such genetic engineering techniques, is the ability to provide crop plants having a convenient source of wax esters. Wax esters are required in a variety of industrial applications, including pharmaceuticals, cosmetics, detergents, plastics, and lubricants. Such products, especially long chain wax esters have previously been available from the sperm whale, an endangered species, or more recently, from the desert shrub, jojoba. Neither of these sources provides a convenient supply of wax esters. Thus, in order to obtain a reliable source of such compounds, transformation of crop plants, which are easily manipulated in terms of growth, harvest and extraction of products, is desirable.

In order to obtain such transformed plants, however, the genes responsible for the biosynthesis of the desired wax ester products must first be obtained. Wax ester production results from the action of at least two enzymatic activities, fatty acyl reductase and fatty acyl:fatty alcohol acyltransferase, or wax synthase. In addition, a β-ketoacyl-ACP synthase may also be involved in wax biosynthesis by providing very long chain fatty acyl-CoA substrates for the reductase and wax synthase enzymatic reaction. Preliminary studies with such enzymes and extensive analysis and purification of a fatty acyl reductase, indicate that these proteins are associated with membranes, however the enzyme responsible for the fatty acyl:fatty alcohol ligation reaction in wax biosynthesis has not been well characterized. Thus, further study and ultimately, purification of this enzyme is needed so that the gene sequences which encode the enzymatic activity may be obtained.

It is desirable, therefore, to devise a purification protocol whereby the wax synthase protein may be obtained and the amino acid sequence determined and/or antibodies specific for the wax synthase obtained. In this matter, library screening polymerase chain reaction (PCR) or immunological techniques may be used to identify clones expressing a wax synthase protein. Clones obtained in this manner can be analyzed so that the nucleic acid sequences corresponding to wax synthase activity are identified. The wax synthase nucleic acid sequences may then be utilized in conjunction with fatty acyl reductase proteins, either native to the transgenic host cells or supplied by recombinant techniques, for production of wax esters in host cells.

Relevant Literature

Cell-free homogenates from developing jojoba embryos were reported to have acyl-CoA fatty alcohol acyl transferase activity. The activity was associated with a floating wax pad which formed upon differential centrifugation (Pollard et al. (1979) supra; Wu et al. (1981) supra).

Solubilization of a multienzyme complex from Euglena gracilis having fatty acyl-SCoA transacylase activity is reported by Wildner and Hallick (Abstract from The Southwest Consortium Fifth Annual Meeting, Apr. 22–24, 1990, Las Cruces, N.Mex.).

Ten-fold purification of jojoba acyl-CoA: alcohol transacylase protein is reported by Pushnik et al. (Abstract from The Southwest Consortium Fourth Annual Meeting, Feb. 7, 1989, Riverside, Calif.).

An assay for jojoba acyl-CoA:alcohol transacylase activity was reported by Garver et al. (Analytical Biochemistry (1992) 207:335–340).

WO 93/10241 is directed to plant fatty acyl-CoA:fatty alcohol O-acyltransferases. A jojoba 57 kD protein is identified as the jojoba fatty acyl-CoA:fatty alcohol O-acyltransferase (wax synthase). The present inventors later reported that the 57 kD protein from jojoba is a β-ketoacyl-CoA synthase involved in the biosynthesis of very long chain fatty acids (Lassner et al. (The Plant Cell (1996) 8:281–292).

Photoaffinity labeling of a 57 kD jojoba seed polypeptide postulated to be an acyl-CoA:fatty alcohol acyltransferase was also reported by Shockey et al. (Plant Phys. (1995) 107:155–160).

BRIEF DESCRIPTION OF THE DRAWINGS

FIG. 1 presents results of analysis of wax synthase activity in column fractions from a first wax synthase purification protocol.

FIG. 2 presents results of analysis of wax synthase activity in column fractions from a second wax synthase purification protocol.

FIG. 3 provides the nucleotide sequence SEQ. ID NO. 1 of the PCR product from primers WSPEP14-F1 and WSPEP33-R2 (FIG. 3A) and the complete nucleotide sequence of SEQ. ID NO. 2 of a fatty acyl-CoA:fatty alcohol O-acyltransferase from jojoba inferred from 5' and 3' RACE products (FIG. 3B).

SUMMARY OF THE INVENTION

Figure 1A:
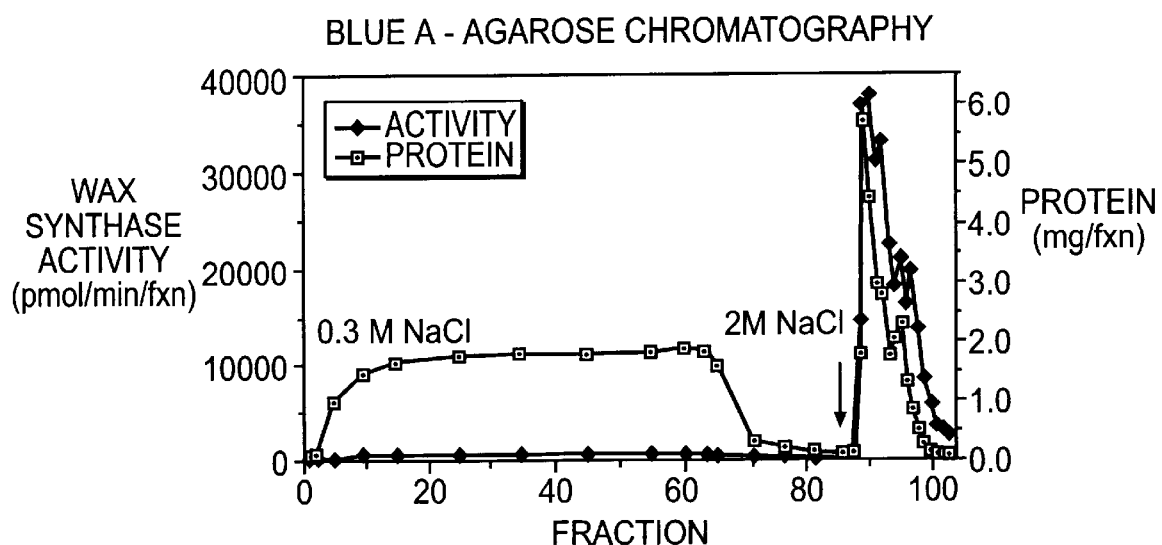
FIG. 1A provides results of Blue A agarose chromatography.
Figure 1B:
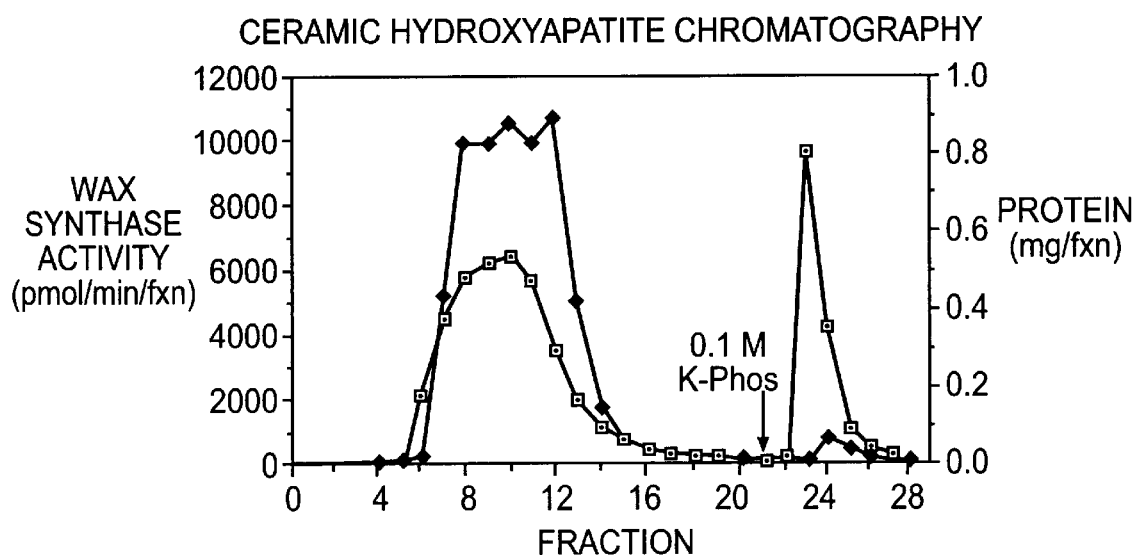
FIG. 1B provides results of ceramic hydroxyapatite chromatography.
Figure 1C:
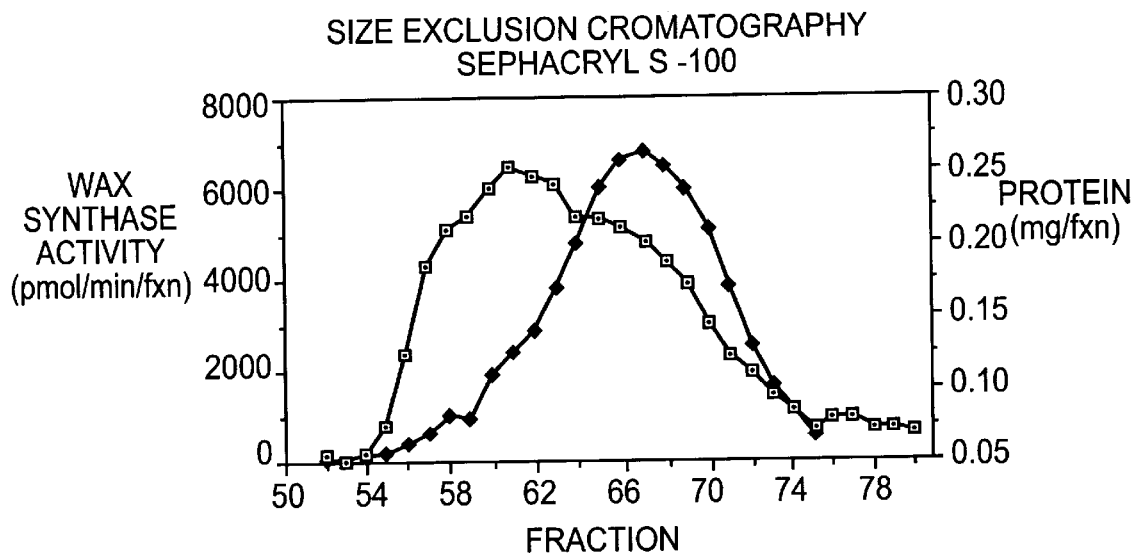
FIG. 1C provides results of sephracryl S-100 size exclusion chromatography.
Figure 1D:
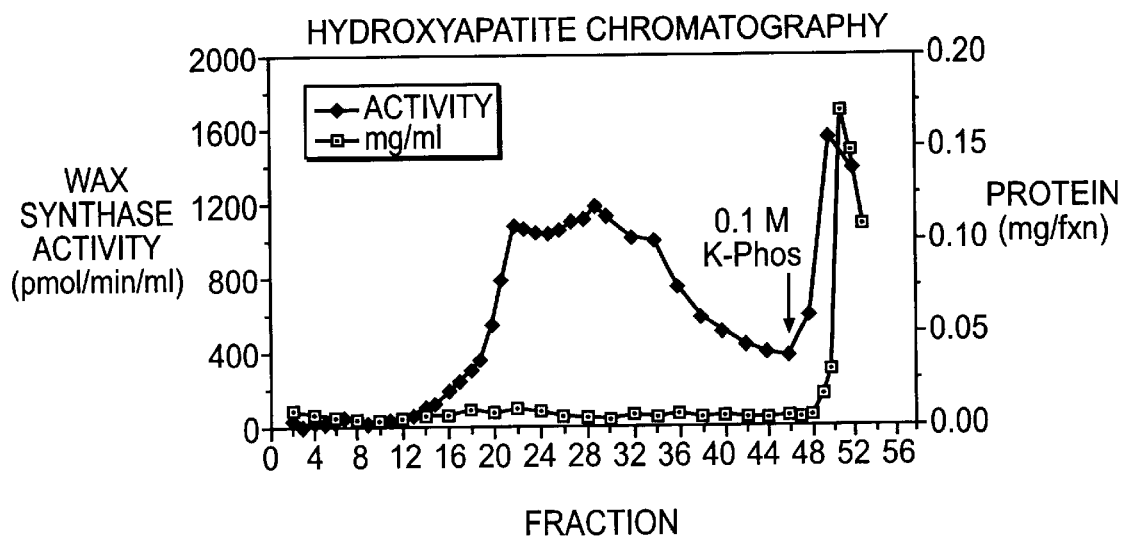
FIG. 1D provides results of hydroxyapatite chromatography.

By this invention, nucleic acid sequences encoding fatty acyl-CoA: fatty alcohol O-acyltransferase protein (fatty alcohol acyltransferase, E.C.2.3.1.75), are provided, wherein said protein is active in the formation of wax esters from fatty alcohol and fatty acyl substrates. This fatty acyl-CoA: fatty alcohol O-acyltransferase is also referred to herein as "wax synthase". The wax synthase of this invention may be active with a variety of fatty acyl and fatty alcohol substrates, including acyl-CoAs and acyl-ACPs. The carbon chain length of these substrates may vary, although a given wax synthase may show preference for acyl and alcohol substrates having a specific chain length or may be active with acyl and alcohol substrates having a wide range with respect to carbon chain length.

In general, the wax synthase of this invention has activity towards at least those acyl and alcohol substrates having a chain length of from 8 to 26 carbons, although other acyl or alcohol substrates may be tested and further activities discovered. In addition, having obtained the wax synthase protein of this invention, further manipulations are now possible as described in further detail below. These manipulations may lead to production or discovery of other related wax synthases.

In one important aspect of this invention, nucleic acid sequences are provided which encode for wax synthase. Methods are described whereby these sequences may be identified and obtained from the amino acid sequences of the wax synthase proteins of this invention. Uses of structural gene sequences for isolation of other wax synthase sequences, as well as in recombinant constructs for transcription of wax synthase nucleic acid sequences and/or expression of wax synthase proteins in host cells are described. Uses of other nucleic acid sequences associated with wax synthase protein are also considered, such as the use of 5' and 3' noncoding regions.

Thus, this invention encompasses plant wax synthase nucleic acid sequences and the corresponding amino acid sequences, and the use of these nucleic acid sequences in the preparation of oligonucleotides containing wax synthase encoding sequences for analysis and recovery of plant wax synthase gene sequences. The plant wax synthase encoding sequence may encode a complete or partial sequence depending upon the intended use. All or a portion of the genomic sequence, or cDNA sequence, is intended.

Of special interest are recombinant DNA constructs which provide for transcription or transcription and translation (expression) of the plant wax synthase sequences. In particular, constructs which are capable of transcription or transcription and translation in plant host cells are preferred. For some applications a reduction in plant wax synthase may be desired. Thus, recombinant constructs may be designed having the plant wax synthase sequences in a reverse orientation for expression of an anti-sense sequence or use of co-suppression, also known as "transwitch", constructs may be useful. Such constructs may contain a variety of regulatory regions including transcriptional initiation regions obtained from genes preferentially expressed in plant seed tissue. For some uses, it may be desired to use the transcriptional and translational initiation regions of the wax synthase gene either with the wax synthase encoding sequence or to direct the transcription and translation of a heterologous sequence.

In yet a different aspect, this invention relates to a method for producing a wax synthase in a host cell or progeny thereof via the expression of a construct in the cell. Cells containing a wax synthase as a result of the production of the plant wax synthase encoding sequence are also contemplated herein. Such constructs may employ other nucleic acid sequences which encode for proteins involved in the production of wax esters and/or various fatty acyl species.

Further, it may be recognized that the wax synthases of this invention may find application in the production of wax esters in such host cells which contain fatty acyl and fatty alcohol substrates of the wax synthase. Such host cells may exist in nature or be obtained by transformation with nucleic acid constructs which encode a fatty acyl reductase. Fatty acyl reductase, or "reductase", is active in catalyzing the reduction of a fatty acyl group to the corresponding alcohol. Co-pending U.S. patent applications 07/659,975 (filed Feb. 22, 1991), 07/767,251 (filed Sep. 27, 1991) and 07/920,430 (filed Jul. 31, 1992), which are hereby incorporated by reference, are directed to such reductase proteins. This information is also provided in published PCT patent application WO 92/14816. In addition, other sources of wax synthase proteins are described herein which are also desirable sources of reductase proteins.

Especially considered in this aspect of the invention, are plant cells which contain the preferred alcohol substrates of a jojoba wax synthase described herein. A method of providing plant cells with such alcohol substrates is considered wherein said cells are transformed with recombinant nucleic acid constructs which encode a fatty acyl reductase nucleic acid sequence. Thus, plant hosts which do not normally contain significant amounts of the alcohol substrates utilized by wax synthase, may be transformed with a reductase construct such that the alcohols are produced. In this manner, the fatty acyl groups present in the host cell will also provide the source of fatty alcohol substrate utilized by wax synthase in the synthesis of wax esters. Depending on the specificities of the wax synthase and reductase proteins, one recognizes that in this manner, plant cells may be obtained which produce a variety of desirable wax ester products. Such products will have different properties depending on the chain length and degree of saturation of the fatty alcohol and fatty acyl groups. Thus, the wax ester products produced according to the methods herein may be recovered from the host cells and are also considered in this invention.

Also considered in this invention are the modified plants, seeds and wax esters obtained by expression of the plant wax synthase sequences and proteins of this invention.

DETAILED DESCRIPTION OF THE INVENTION

In accordance with the subject invention, nucleic acid sequences are provided which encode for amino acids, such as a protein, polypeptide or peptide fragment, which are active in catalyzing the esterification of a fatty alcohol by a fatty acyl group to produce a wax ester. Such proteins are known as fatty acyl-CoA: fatty alcohol acyltransferase (E.C. 2.3.1.75). The acyl-CoA: alcohol acyltransferase of this invention is also referred to hereafter as "wax synthase".

Although typically referred to as an acyl-CoA: alcohol acyltransferase, the wax synthases of this invention may demonstrate activity towards a variety of acyl substrates, including fatty acyl-CoA and fatty acyl-ACP molecules. In addition, both the acyl and alcohol substrates acted upon by the wax synthase may have varying carbon chain lengths and degrees of saturation, although the wax synthase may demonstrate preferential activity towards certain molecules.

Many different organisms produce wax esters from alcohol and acyl substrates and are desirable sources of a wax synthase protein of this invention. For example, plants produce epidermal, or cuticular wax (Kolattukudy (1980) in The Biochemistry of Plants (Stumpf, P. K. and Conn, E. E., eds.) Vol.4, p. 571–645), and the desert shrub, jojoba, produces a seed storage wax (Ohlrogge et al. (Lipids (1978) 13:203–210). Wax synthesis has also been observed in various species of bacteria, such as Acinetobacter (Fixter et al. (1986). J. Gen. Microbiol. 132:3147–3157) and Micrococcus (Lloyd (1987) Microbios 52:29–37), and by the unicellular organism, Euglena (Khan and Kolattukudy (1975) Arch. Biochem. Biophys. 170:400–408). In addition, wax production and wax synthase activity have been reported in microsomal preparations from bovine meibomian glands (Kolattukudy et al. (1986) J. Lipid Res. 27:404–411), avian uropygial glands, and various insect and marine organisms. Consequently, many different wax esters which will have various properties may be produced by the wax synthases of this invention, and the activity of the enzyme and type of wax ester produced may depend upon the available substrate or the substrate specificity of the particular wax synthase of interest.

To obtain a reliable source of a wax synthase protein for use in esterification reactions, it is desirable to isolate nucleic acid sequences associated with the wax synthase such that these sequences may be cloned into host cells for the production of the wax synthase enzyme. For example, one may clone nucleic acid sequences encoding a wax synthase protein into vectors for expression in E. coli cells to provide a ready source of the wax synthase protein. The wax synthase protein so produced may also be used to raise antibodies against wax synthase proteins for use in identification and purification of related wax synthase proteins from various sources, especially from plants. In addition, further study of the wax synthase protein may lead to site-specific mutagenesis reactions to further characterize and improve its catalytic properties or to alter its fatty alcohol or fatty acyl substrate specificity. A wax synthase with altered substrate specificity may find application in conjunction with other FAS enzymes.

Prior to the instant invention, nucleic acid and amino acid sequences of wax synthase proteins were not known. Thus, in order to obtain the nucleic acid sequences associated with wax synthase, it was necessary to first purify the protein from an available source and determine at least partial amino acid sequence so that appropriate probes useful for isolation of wax synthase nucleic acid sequences could be prepared.

The desert shrub, Simmondsia chinensis (jojoba) was identified as a source of a candidate wax synthase protein. Initial studies reveal that the jojoba wax synthase is an integral membrane protein and hydrophobic in nature. In general, membrane associated proteins are difficult to purify as they tend to lose enzymatic activity when they are solubilized, i.e. separated from the membrane environment in which they normally function. Techniques that have been used to solubilize integral membrane proteins include addition of detergents or organic solvents to a preparation of a suitable membrane fraction. Further conventional purification techniques, such as precipitation, ion-exchange, gel-filtration and affinity chromatography may then be utilized, assuming the desired protein still retains functional activity that can be measured using a specific enzymatic assay.

Typically, as a first step towards obtaining a solubilized membrane protein, a microsomal membrane preparation which comprises wax synthase activity is desired. Standard microsomal membrane preparation utilize differential centrifugation of a cell-free homogenate (CFH) to yield a membrane fraction which is free of whole cells, nuclei and soluble protein (See, for example Mooré et al. (1987) Biological Membranes: A Practical Approach. pp. 37–72, eds. Finalay and Evans). With oilseeds, initial centrifugation steps typically yield a pellet, supernatant and a floating fat pad, and microsomal membranes may then be recovered by further centrifugation of the supernatant.

A protocol is described in U.S. Pat. No. 5,403,918, whereby a jojoba membrane fraction was obtained with good recovery of enzyme activity associated with fatty acyl reductase, another enzyme involved in the formation of wax esters in jojoba. The method also provides membrane fractions having wax synthase activity as described in detail in the examples which follow. In addition, microsomal membrane preparations from jojoba are also described in Lassner et al. (supra). Other procedures are known to those in the art and may be utilized to obtain similar membrane preparations. In addition, methods to assay for wax synthase activity in such preparations are described in Example 1.

A critical stage for further enzyme characterization and purification is that of obtaining solubilized wax synthase protein that is separated from its native lipid bilayer membrane environment, but retains substantial amounts of measurable wax synthase enzymatic activity. The removal of integral membrane proteins from the lipid bilayer is typically accomplished using amphiphilic detergents in aqueous solution, although organic solvents have also been used in a few cases. Many different detergents and methods of solubilization of membrane proteins are known to those skilled in the art, and are also reviewed by Neugebauer (Methods Enzymol. (1990) 182:239–253) and Hjelmiland (Methods Enzymol. (1990) 182:253–264).

Often, detergents which are used to solubilize membrane proteins are found to inhibit the enzymatic activity of a desired protein. Several detergents were tested for solubilization of jojoba wax synthase, including CHAPS (3-[(3-cholamidopropyl)-dimethyl-ammonio]-1-propanesulfonate), which was demonstrated in U.S. Pat. No. 5,403,918 to be useful in purification of a fatty acyl reductase from jojoba. All were found to inhibit wax synthase enzymatic activity. Although strong inhibition by CHAPS was observed at concentrations above the CMC, it was found that addition of phospholipids, such as L-phosphatidyl choline, and adjustment of the CHAPS concentration from 1.0% to 0.2%, i.e. to below the CMC, results in reconstitution of a portion of the wax synthase activity. The primary requirement for reconstitution of wax synthase activity in the presence of phospholipids during the removal or dilution of the detergent, so that the wax synthase protein is incorporated into phospholipids vesicles. This differs from the protocol developed for reconstitution of jojoba reductase activity, which does not require addition of phospholipids. Thus, if phospholipids are present in a wax synthase preparation, such as that from a microsomal membrane fraction, activity may be detected simply by removal or dilution of detergent. However, in further purified wax synthase preparations, phospholipids must be added to detect activity. Optimum activity recovery is obtained when a ratio of CHAPS to PL is 2.8/1 (w/w) in the assay. A method of reconstitute and assay wax synthase activity in solubilized wax synthase preparations is described in Example 1.

Having obtained solubilized wax synthase protein, it can be seen that further experiments to characterize the enzyme as to substrate specificity, cofactor requirements and possible activity inhibiting agents may now be conducted. For example, it has been found that the jojoba wax synthase of this invention has a broad range of acyl substrates, including acyl-ACP and acyl-CoA molecules. In addition, the acyl and fatty alcohol substrates may have a broad size range with respect to carbon chain length. For example, activity was tested using substrates having carbon chain lengths of from C12 to C24, and all were shown to be utilized by the enzyme. In addition, activity was shown with fatty acyl and fatty alcohols having varying degrees of unsaturation.

Chromatography techniques may be utilized to provide enriched preparations of plant wax synthase. One such purification step involves chromatography over an immobilized reactive dye matrix, such as the Cibacron Blue F3GA (Blue A) used in this invention. The jojoba wax synthase activity binds to such a column when loaded in a buffer containing approximately 0.3 M NaCl, while greater than approximately 85% of other protein passes through or is removed in subsequent washes. As described in U.S. Pat. No. 5,403,918, reductase activity is also bound to the Blue A column under such conditions. It is demonstrated herein that approximately 70% of the wax synthase activity loaded to a Blue A column can be recovered by elution with a 2.0 M NaCl buffer wash. The jojoba reductase and β-ketoacyl-CoA synthase (KCS) proteins are also present in this Blue A eluate.

Further purification of the Blue A eluate is obtained by loading the sample onto a crystalline hydroxyapatite (HA) column. Wax synthase activity does not bind to the column and is found in the flow through and wash. The majority of the reductase and KCS activities bind to the column, as does the majority of the protein in the sample. The HA fraction enriched in wax synthase activity can be used for size exclusion chromatography, and using a Superdex 75 size exclusion column, the jojoba wax synthase protein is estimated to have a molecular weight of 48 kD.

Using such purification techniques, the jojoba wax synthase protein can be recovered as a substantially purified protein preparation and the amino acid sequence can be obtained. Similarly, due to the hydrophobic nature of the fatty alcohol substrates of wax synthase enzymes, other wax synthases would also be predicted to be associated with membranes in their native cells, and thus purification techniques described herein for jojoba wax synthase, may also be useful in recovery of purified preparation of other wax synthase proteins.

For example, Euglena gracilis produces waxes through the enzymatic actions of a fatty acyl-CoA reductase and a fatty acyl-CoA alcohol transacylase, or wax synthase. Typically, waxes having carbon chain lengths ranging from 24–32 are detected in this organism. As described above for jojoba, the Euglena wax synthase enzyme may be solubilized using a CHAPS/NaCl solution, and a partially purified wax synthase preparation is obtained by dye-ligand, HA and size exclusion chromatography.

Acinetobacter species are also known to produce wax ester compositions, although the mechanism is not well defined. As described herein a fatty acyl-CoA alcohol transacylase, or wax synthase activity is detected in Acinetobacter species. The wax synthase activity is solubilized in CHAPS/NaCl, enriched by Blue A column chromatography and may be further purified using such techniques as size exclusion chromatography.

In order to obtain nucleic acid sequences encoding the wax synthase of the present invention, the band containing the purified protein is cut out of an SDS gel to use in amino acid sequencing reactions. In gel digestion was used as opposed to more convenient methods, such as transfer of the protein to nitrocellulose or polyvinylidenedifluoride (PVDF) membranes due to the fact that conditions under which the jojoba wax synthase protein could be blotted and bound to such membranes have not been discovered. A commercial laboratory, W. M. Keck Foundation/Yale University, was provided with gel slices containing purified jojoba wax synthase protein for use in determining amino acid sequences of the jojoba protein by in-gel digest and subsequent protein sequencing. The peptide sequences generated in this manner may be used in PCR gene isolation techniques and cDNA library screening as described in more detail in the following examples.

Further experiments to confirm the identify of the wax synthase may also be desirable, such as expression of the protein in E. coli. The wax synthase may then act on fatty acyl and fatty alcohol substrates in such cells to produce wax esters which may be detected by various analytical methods. If the host cells do not contain the alcohol substrate of the wax synthase, activity may be verified by assaying cell extracts. Alternatively, wax synthase protein may be prepared by in vitro translation using wax synthase nucleic acid sequences and commercially available translation kits. Addition of microsomal membrane preparations to the in vitro translation sample may be necessary to obtain active wax synthase protein if membrane insertion is critical to activity. Other testing may include immunological assays, whereby antibodies specific for the candidate protein are prepared and found to inhibit wax synthase activity in protein preparations.

Thus, was described in more detail in the examples below, nucleic acid sequences are isolated using amino acid sequences determined for the proteins associated with wax synthase activity, both to confirm the identity of an wax synthase protein and to provide for transcription of the sequences and/or expression of the protein in host cells, either prokaryotic or eukaryotic.

As the wax synthase is a membrane bound protein, it may be desirable to express a candidate protein in a plant cell in order to verify the activity. Electroporation or bombardment of plant tissue for transient expression may be useful for this purpose. Ultimately, stable plant expression in a plant which produces substrates recognized by this enzyme is desired. If a plant targeted for transformation with wax synthase sequences does not naturally contain the fatty alcohol and fatty acyl ester substrates of this enzyme, a plant extract may be prepared and assayed for wax synthase activity by adding substrates of the wax synthase to the extract. Constructs and methods for transformation of plant hosts with wax synthase sequences are discussed in more detail below.

The wax synthase nucleic acids of this invention may be genomic or cDNA or may be isolated from cDNA or genomic libraries or directly from isolated plant DNA. As described in more detail in the examples below, a method for obtaining nucleic acid sequence for the jojoba wax synthase by PCR from primers specific for the disclosed jojoba wax synthase peptides is provided herein.

Wax synthase nucleic acid sequences of this invention include those corresponding to the jojoba wax synthase protein, as well as sequences obtainable from the jojoba protein or nucleic acid sequences. By "corresponding" is meant nucleic acid sequences, either DNA or RNA, including those which encode jojoba wax synthase protein or a portion thereof, regulatory sequences found 5' or 3' to said encoding sequences which direct the transcription or transcription and translation (expression) of the wax synthase in jojoba embryos, intron sequences not present in the cDNA, as well as sequences encoding any leader or signal peptide of a precursor wax synthase protein that may be required for insertion into the endoplasmic reticulum membrane, but is not found in the mature wax synthase enzyme.

By sequences "obtainable" from the jojoba sequence or protein, is intended any nucleic acid sequences associated with a desired wax synthase protein that may be synthesized from the jojoba wax synthase amino acid sequence, or alternatively identified in a different organism, and isolated using as probes jojoba wax synthase nucleic acid sequences or antibodies prepared against the jojoba wax synthase protein. In this manner, it can be seen that sequences of these other wax synthases may similarly be used to isolate nucleic acid sequences associated with wax synthase proteins from additional sources.

For isolation of nucleic acid sequences, cDNA or genomic libraries may be prepared using plasmid or viral vectors and techniques well known to those skilled in the art. Useful nucleic acid hybridization and immunological methods that may be used to screen for the desired sequences are also well known to those in the art and are provided, for example in Maniatis, et al. (Molecular Cloning: A Laboratory Manual, Second Edition (1989) Cold Spring Harbor Laboratory, Cold Spring Harbor, N.Y.).

Typically, a sequence obtainable from the use of nucleic acid probes will show 60–70% sequence identity between the target sequence and the given sequence encoding a wax synthase enzyme of interest. However, lengthy sequences with a little as 50–60% sequence identity may also be obtained. The nucleic acid probes may be a length fragment of the nucleic acid sequence, or may also be a shorter, oligonucleotide probe. When longer nucleic acid fragments are employed as probes (greater than about 100 bp), one may screen at lower stringencies in order to obtain sequences from the target sample which have 20–50% deviation (i.e., 50–80 sequence homology) from the sequences used as probe. Oligonucleotide probes can be considerably shorter than the entire nucleic acid sequence encoding a wax synthase enzyme, but should be at least about 10, preferably at least about 15, and more preferably at least about 20 nucleotides. A higher degree of sequence identity is desired when shorter regions are used as opposed to longer regions. It may thus be desirable to identify enzyme active sites where amino acid sequence identity is high to design oligonucleotide probes for detecting homologous genes.

To determine if a related gene may be isolated by hybridization with a given sequence, the sequence is labeled to allow detection, typically using radioactivity, although other methods are available. The labeled probe is added to a hybridization solution, and incubated with filters containing the desired nucleic acids, either Northern or Southern blots (to screen desired sources for homology), or the filters containing cDNA or genomic clones to be screened. Hybridization and washing conditions may be varied to optimize the hybridization of the probe to the sequences of interest. Lower temperatures and higher salt concentrations allow for hybridization of more distantly related sequences (low stringency). If background hybridization is a problem under low stringency conditions, the temperature can be raised either in the hybridization or washing steps, and/or salt content lowered to improve detection of the specific hybridizing sequence. Hybridization and washing temperatures can be adjusted based on the estimated melting temperature of the probe as discussed in Beltz, et al. (Methods in Enzymology (1983) 100:266–285).

A useful probe and appropriate hybridization and washing conditions having been identified as described above, cDNA or genomic libraries are screened using the labeled sequences and optimized conditions. The libraries are first plated onto a solid agar medium, and the DNA lifted to an appropriate membrane, usually nitrocellulose or nylon filters. These filters are then hybridized with the labeled probe and washed as discussed above to identify clones containing the related sequences.

For immunological screening, antibodies to the jojoba wax synthase can be prepared by injecting rabbits or mice with the purified protein. Methods of preparing antibodies are well known to those in the art, and companies which specialize in antibody production are also available. Either monoclonal or polyclonal antibodies can be produced, although typically polyclonal antibodies are more useful for gene isolation.

To screen desired plant species, Western analysis is conducted to determine that a related protein is present in a crude extract of the desired plant species, that cross-reacts with the antibodies to the jojoba wax synthase. This is accomplished by immobilization of the plant extract proteins on a membrane, usually nitrocellulose, following electrophoresis, and incubation with the antibody. Many different systems for detection of the antibody/protein complex on the nitrocellulose filters are available, including radiolabeling of the antibody and second antibody/enzyme conjugate systems. Some of the available systems have been described by Oberfelder (Focus (1989) BRL/Life Technologies, Inc. 11:1–5). If initial experiments fail to detect a related protein, other detection systems and blocking agents may be utilized. When cross-reactivity is observed, genes encoding the related proteins can be isolated by screening expression libraries representing the desired plant species. Expression libraries can be constructed in a variety of commercially available vectors, including lambda gt11, as described in Maniatis, et al. (supra).

The clones identified as described above using DNA hybridization or immunological screening techniques are then purified and the DNA isolated and analyzed using known techniques. In this manner, it is verified that the clones encode a related wax synthase protein. Other wax synthases may be obtained through the use of the "new" wax synthase in the same manner as the jojoba wax synthase was used.

It will be recognized by one of ordinary skill in the art that wax synthase nucleic acid sequences of this invention may be modified using standard techniques of site specific mutation or PCR, or modification of the sequence may be accomplished in producing a synthetic nucleic acid sequence. These modified sequences are also considered wax synthase nucleic acid sequence of this invention. For example, wobble positions in codons may be changed such that the nucleic acid sequence encodes the same amino acid sequence, or alternatively, codons can be altered such that conservative amino acid substitutions result. In either case, the peptide or protein maintains the desired enzymatic activity and is thus considered part of the instant invention.

A nucleic acid sequence of a wax synthase enzyme of this invention may be a DNA or RNA sequence, derived from genomic DNA, or cDNA, mRNA, or may be synthesized in whole or in part. The gene sequences may be cloned, for example, by isolating genomic DNA from an appropriate source, and amplifying and cloning the sequence of interest using a polymerase chain reaction (PCR). Alternatively, the gene sequences may be synthesized, either completely or in part, especially where it is desirable to provide plant-preferred sequences. Thus, all or a portion of the desired structural gene (that portion of the gene which encodes the wax synthase protein) may be synthesized using codons preferred by a selected host. Host-preferred codons may be determined, for example, from the codons used most frequently in the proteins expressed in a desired host species.

The nucleic acid sequences associated with wax synthase proteins will find many uses. For example, recombinant constructs can be prepared which can be used as probes or will provide for expression of the wax synthase protein in host cells. Depending upon the intended use, the constructs may contain the sequence which encodes the entire wax synthase, or a portion thereof. For example, critical regions of the wax synthase, such as an active site may be identified. Further constructs containing only a portion of the wax synthase sequence which encodes the amino acids necessary for a desired wax synthase activity may thus be prepared.

Useful systems for expression of the wax synthase sequences of this invention include prokaryotic cells, such as E. coli, yeast cells and plant cells, both vascular and nonvascular plant cells being desired hosts. In this manner, the wax synthase protein may be produced to allow further studies, such as site-specific mutagenesis of encoding sequences to analyze the effects of specific mutations on reactive properties of the wax synthase protein.

The DNA sequence encoding a wax synthase of this invention may be combined with foreign DNA sequences in a variety of ways. By "foreign" DNA sequences is meant any DNA sequence which is not naturally found joined to the wax synthase sequence, including DNA sequences from the same organism which are not naturally found joined to wax synthase sequences. Both sense and antisense constructs utilizing wax synthase encoding sequences are considered, wherein sense sequence may be used for expression of wax synthase in a host cell, and antisense sequences may be used to decrease the endogenous levels of a homologous wax synthase protein naturally produced by a target organism. In addition, the wax synthase gene sequences of this invention may be employed in a foreign host in conjunction with all or part of the sequences normally associated with the wax synthase, such as regulatory or membrane targeting sequences.

In its component parts, a DNA sequence encoding wax synthase is combined in a recombinant construct having, in the 5' to 3' direction of transcription, a transcription initiation control region capable of promoting transcription and translation in a host cell, the nucleic acid sequence encoding wax synthase and a transcription termination region. Depending upon the host, the regulatory regions will vary, and may include regions from viral, plasmid or chromosomal genes, or the like. For expression in prokaryotic or eukaryotic microorganisms, particularly unicellular hosts, a wide variety of constitutive or regulatable promoters may be employed. Expression in a microorganism can provide a ready source of the plant enzyme. Among transcriptional initiation regions which have been described are regions from bacterial and yeast hosts, such as E. coli, B. subtilis, Sacchromyces cerevisiae, including genes such as beta-galactosidase, T7 polymerase, tryptophan E and the like.

For the most part, the recombinant constructs will involve regulatory regions functional in plants which provide for expression of the wax synthase gene to produce functional wax synthase protein. The open reading frame, coding for the plant wax synthase or a functional fragment thereof will be joined at its 5' end to a transcription initiation regulatory region such as the wild-type sequence naturally found 5' upstream to the wax synthase structural gene. Numerous other promoter regions from native plant genes are available which provide for a wide variety of constitutive or regulatable expression of structural gene sequences.

In addition to sequences from native plant genes, other sequences can provide for constitutive gene expression in plants, such as regulatory regions associated with Agrobacterium genes, including regions associated with nopaline synthase (Nos), mannopine synthase (Mas), or octopine synthase (Ocs) genes. Also useful are regions which control expression of viral genes, such as the 35S and 19S regions of cauliflower mosaic virus (CaMV). The term constitutive as used herein does not necessarily indicate that a gene is expressed at the same level in all cell types, but that the gene is expressed in a wide range of cell types, although some variation in abundance is often detectable. Other useful transcriptional initiation regions preferentially provide for transcription in certain tissues or under certain growth conditions, such as those from napin, seed or leaf ACP, the small subunit of RUBISCO, and the like.

In embodiments wherein the expression of the wax synthase protein is desired in a plant host, the use of all or part of the complete plant wax synthase gene may be desired, namely the 5' upstream non-coding regions (promoter) together with the structural gene sequence and 3' downstream non-coding regions may be employed. If a different promoter is desired, such as a promoter native to the plant host of interest or a modified promoter, i.e., having transcription initiation regions derived from one gene source and translation initiation regions derived from a different gene source or enhanced promoters, such as double 35S CaMV promoters, the sequences may be joined together using standard techniques. Additionally, 5' untranslated regions from highly expressed plant genes may be useful to provide for increased expression of the wax synthase proteins described herein.

The DNA constructs which provide for wax synthase expression in plants may be employed with a wide variety of plant life, particularly, plants which produce the fatty acyl-CoA substrates of the wax synthase enzyme, such as Brassica. Other plants of interest produce desirable fatty acyl substrates, such as medium or long chain fatty acyl molecules, and include but are not limited to rapeseed (canola varieties), sunflower, safflower, cotton, Cuphea, soybean, peanut, coconut and oil palms, and corn. Of particular interest is the use of such constructs in high erucic acid varieties of rapeseed Brassica (HEAR) for production of long-chain liquid waxes. Further uses envisioned for HEAR plants includes the production of varieties containing substantially increased levels of erucic acid as the result of providing an additional wax "sink" for the erucic acid, which is normally stored in the seed TAG.

As to the fatty alcohol substrate of the wax synthase enzyme, other than jojoba, seed plants are not known to produce large quantities of fatty alcohols, although small amounts of this substrate may be available to the wax synthase enzyme. Therefore, in conjunction with the wax synthase constructs of this invention, it is desirable to provide the target host cell with the capability to produce fatty alcohols from the fatty acyl molecules present in the host cells. For example, a plant fatty acyl reductase and methods to provide for expression of the reductase enzymes in plant cells are described in U.S. Pat. No. 5,370,996. The nucleic acid sequence and translated amino acid sequence of the jojoba reductase is provided in FIG. 1 of that patent. Thus, by providing both the wax synthase and reductase proteins to the host plant cell, wax esters may be produced from the fatty alcohol and fatty acyl substrates. Furthermore, expression of $\beta$-ketoacyl-CoA synthase in conjunction with expression of wax synthase and reductase proteins is considered in the present invention. In this manner, the production of very long chain fatty acid substrates of these enzymes may be increased in the target plant species.

In addition to the jojoba reductase, reductase enzymes from other organisms may be useful in conjunction with the wax synthases of this invention. Other potential sources of reductase enzymes include Euglena, Acinetobacter, Micrococcus, certain insects and marine organisms, and specialized mammalian or avian tissues which are known to contain wax esters, such as bovine meibomian glands or ovian uropygial glands. Other potential sources of reductase proteins may be identified by their ability to produce fatty alcohols or, if wax synthase is also present, wax esters.

The wax synthase and reductase sequences may be provided during the same transformation event, or alternatively, two different transgenic plant lines, one having wax synthase constructs and the other having reductase constructs may be produced by transformation with the various constructs. These plant lines may then be crossed using known plant breeding techniques to provide wax synthase and reductase containing plants for production of wax ester products.

Furthermore, other nucleic acid sequences encoding for enzymes involved in the formation of very long chain fatty acids may also find use in the DNA constructs of the present invention for the production of wax esters in a plant host. Such nucleic acid sequences are known in the art and are as described in U.S. Pat. No. 5,679,881. For example, as described in the examples below, the wax synthase of the present invention is used in plant expression constructs in conjunction with nucleic acid sequences encoding for a fatty acid elongase (described in U.S. Pat. No. 5,679,881, the entirety of which is incorporated herein by reference) and an acyl-CoA reductase (described in U.S. Pat. No. 5,403,918, the entirety of which is incorporated herein by reference). Such plant expression constructs provide for the production of wax esters in transgenic Arabidopsis thaliana plants.

For applications leading to wax ester production, 5' upstream non-coding regions obtained from genes regulated during seed maturation are desired, especially those preferentially expressed in plant embryo tissue, such as regions derived from ACP, oleosin (Lee and Huang (1981) *Plant Physiol.* 96:1395–1397) and napin regulatory regions. Transcription initiation regions which provide for preferential expression in seed tissue, i.e., which are undetectable in other plant parts, are considered desirable for wax ester production in order to minimize any disruptive or adverse effects of the gene product in other plant parts. Further, the seeds of such plants may be harvested and the lipid reserves of these seeds recovered to provide a ready source of wax esters. Thus, a novel seed product may be produced in oilseed plants which, absent transformation with wax synthase constructs as described herein, are not known to produce wax esters as a component of their seed lipid reserves.

Such "seed-specific promoters" may be obtained and used in accordance with the teachings of U.S. Pat. No. 5,420,034, and U.S. Pat. No. 5,430,194. In addition, where plant genes, such as the jojoba reductase and wax synthases are expressed, it may be desirable to use the entire plant gene, including 5' and 3' regulatory regions and any introns that are present in the encoding sequence, for expression of the jojoba genes in a transformed plant species, such as Arabidopsis or Brassica.

Regulatory transcription termination regions may be provided in recombinant constructs of this invention as well. Transcription termination regions may be provided by the DNA sequence encoding the plant wax synthase or a convenient transcription termination region derived from a different gene source, especially the transcription termination region which is naturally associated with the transcription initiation region. The transcript termination region will contain at least about 0.5 kb, preferably about 1–3 kb of sequence 3' to the structural gene from which the termination region is derived.

Additional plant gene regions may be used to optimize expression of wax synthase and reductase genes in plant tissues. For example, 5' untranslated regions of highly expressed genes, such as that of the small subunit (SSU) of RuBP-carboxylase, inserted 5' to DNA encoding sequences may provide for enhanced translation efficiency. Portions of the SSU leader protein encoding region (such as that encoding the first 6 amino acids) may also be used in such constructs. In addition, for applications where targetting to plant plastid organelles is desirable, transit peptide encoding sequences from SSU or other nuclear-encoded chloroplast proteins may be used in conjunction with wax synthase and reductase sequences.

Depending on the method for introducing the DNA expression constructs into the host cell, other DNA sequences may be required. Importantly, this invention is applicable to dicotyledyons and monocotyledons species alike and will be readily applicable to new and/or improved transformation and regeneration techniques.

In developing the recombinant construct, the various components of the construct or fragments thereof will normally be inserted into a convenient cloning vector which is capable of replication in a bacterial host, e.g., *E. coli*. Numerous vectors exist that have been described in the literature. After each cloning, the plasmid may be isolated and subjected to further manipulation, such as restriction, insertion of new fragments, ligation, deletion, insertion, resection, etc., so as to tailor the components of the desired sequence. Once the construct has been completed, it may then be transferred to an appropriate vector for further manipulation in accordance with the manner of transformation of the host cell.

Normally, included with the recombinant construct will be a structural gene having the necessary regulatory regions for expression in a host and providing for selection of transformant cells. The gene may provide for resistance to a cytotoxic agent, e.g. antibiotic, heavy metal, toxin, etc., complementation providing prototrophy to an auxotrophic host, viral immunity or the like. Similarly, genes encoding enzymes providing for production of a compound identifiable by color change, such as GUS, or luminescence, such as luciferase are useful. Depending upon the number of different host species the expression construct or components thereof are introduced, one or more markers may be employed, where different conditions for selection are used for the different hosts.

In addition to the sequences providing for transcription of wax synthase sequences, the DNA constructs of this invention may also provide for expression of an additional gene or genes, whose protein product may act in conjunction with the wax synthase to produce a valuable end product. For example, as discussed above, DNA constructs which provide for expression of wax synthase and a fatty acyl reductase so that wax esters may produced in transformed hosts, are considered in this invention. Furthermore, production of different wax esters having varying carbon chain lengths and degrees of saturation is desired and may be provided by transforming host plants having fatty alcohol or fatty acy substrates of varying chain lengths. Such plants may be provided, for example, by methods described in the published international patent application number PCT WO 91/16421, which describes various thioesterase genes and methods of using such genes to produce fatty acyl substrates having varying chain lengths in transformed plant hosts.

Furthermore, to optimize the production of wax esters in oilseed plant hosts, one may wish to decrease the production of the triacylglyceride oils that are normally produced in the seeds of such plants. One method to accomplish this is to antisense a gene critical to this process, but not necessary for the production of wax esters. Such gene targets include diacylglycerol acyltransferase, and other enzymes which catalyse the synthesis of triacylglycerol. Additionally, it may be desirable to provide the oilseed plants with enzymes which may be used to degrade wax esters as a nutrient source, such as may be isolated from jojoba or various other wax producing organisms. In this manner, maximal production of wax esters in seed plant hosts may be achieved.

The wax esters produced in the methods described herein may be harvested using techniques for wax extraction from jojoba or by various production methods used to obtain oil products from various oilseed crops. The waxes thus obtained will find application in many industries, including pharmaceuticals, cosmetics, detergents, plastics, and lubricants. Applications will vary depending on the chain length and degree of saturation of the wax ester components. For example, long chain waxes having a double band in each of the carbon chains are liquid at room temperature, whereas waxes having saturated carbon chain components, may be solid at room temperature, especially if the saturated carbon chains are longer carbon chains.

The method of transformation is not critical to the instant invention; various methods of plant transformation are currently available. As newer methods are available to transform crops, they may be directly applied hereunder. For example, many plant species naturally susceptible to Agrobacterium infection may be successfully transformed via tripartite or binary vector methods of Agrobacterium mediated transformation. Other sequences useful in providing for transfer of nucleic acid sequences to host plant cells may be derived from plant pathogenic viruses or plant transposable elements. In addition, techniques of microinjection, DNA particle bombardment, electroporation have been developed which allow for the transformation of various monocot and dicot plant species.

The invention now being generally described, it will be more readily understood by reference to the following examples, which are included for purposes of illustration only and are not intended to limit the invention unless so states.

EXAMPLES

Example 1

Wax synthase Assays

Methods to assay for wax synthase activity in microsomal membrane preparations or solubilized protein preparations are described.

A. Radiolabeled Material

The substrate generally used in the wax synthase assays, [1-$^{14}$C]palmitoyl-CoA, is purchased from Amersham (Arlington Heights, Ill.). Other chain length substrates were synthesized in order to perform chain length specification studies. Long chain [1-$^{14}$C] fatty acids (specific activity 51–56 Ci/mole), namely 11-cis-eicosenoic acid, 13-cis-docosenoic acid and 15-cis-tetracosenoic acid are prepared by the reaction of potassium [$^{14}$C]cyanide with the corresponding alcohol mesylate, followed by the base hydrolysis of the alcohol nitrile to the free fatty acid. The free fatty acids are converted to their methyl esters with ethereal diazomethane, and purified by preparative silver nitrate thin layer chromatography (TLC). The fatty acid methyl esters are hydrolyzed back to the free fatty acids. Radiochemical purity is assessed by three TLC methods: normal phase silica TLC, silver nitrate TLC, and C18 reversed phase TLC. Radiochemical purity as measured by these methods was 92–98%. Long chain [1-$^{14}$C] acyl-CoAs are prepared from the corresponding [1-$^{14}$C] fatty acids by the method of Young and Lynen (*J. Bio. Chem.* (1969) 244:377), to a specific activity of 10 Ci/mole. [1-$^{14}$C]hexadecanal is prepared by the dichromate oxidation of [1-$^{14}$C]hexadecan-1-ol, according to a micro-scale modification of the method of Pletcher and Tate (*Tet. Lett.* (1978) 1601–1602). The product is purified by preparative silica TLC, and stored as a hexane solution at −70° C. until use.

B. Assay for Wax synthase Activity in a Microsomal Membrane Preparation

Wax synthase activity in a microsomal membrane preparation is measured by incubation of 40 μM [1-$^{14}$C]acyl-CoA (usually palmitoyl-CoA, sp. act. 5.1–5.6 mCi/mmol) and 200 mM oleyl alcohol with the sample to be assayed in a total volume of 0.25 ml. The incubation mixture also contains either 25 mM HEPES (4-[2-hydroxyethyl]-1-piperazineethane-sulfonic acid), pH 7.5, as the buffering agent with 20% w/v glycerol, 1 mM DTT, 0.5 M NaCl or 25 mM Tricine-NaOH, pH 7.8, as the buffering agent with 0.28M NaCl, 10% glycerol, and 2 mM β-mercaptoethanol. Initial studies were performed with the first buffer system, when the pH was chosen to accomodate the preference of the acyl-CoA reductase enzyme. Membrane preparations were later changed to the second buffer system to accomodate the higher pH optimum of wax synthase.

A substrate mixture is prepared in a glass vial, with oleyl alcohol being added immediately before use, and is added to samples. Incubation is carried out at 30° C. for up to one hour. The assay is terminated by placing the assay tube on ice and immediately adding 0.25 ml isopropanol:acetic acid (4:1 v/v). Unlabeled wax esters (0.1 mg) and oleyl alcohol (0.1 mg) are added as carriers. The [1-$^{14}$C] lipids are extracted by the scaled-down protocol of Hara and Radin (*Anal. Biochem.* (1978) 90:420). Two ml of hexane/isopropanol (3:2, v/v) is added to the terminated assay. The sample is vortexed, 1 ml of aqueous sodium sulphate solution (6.6% w/v) is added, and the sample is again vortexed.

C. Assay for Solubilized Wax synthase Activity

Solubilized wax synthase is assayed using up to 50 μl sample in a 250 μl assay that contains 40 μM 1-$^{14}$-16:0 CoA (5 Ci/mol), 200 μM 18:1-OH, 0.07% soybean phospholipid (Sigma, P-3644), 0.2% CHAPS, 280 mM NaCl, 25 mM Tricine-NaOH, pH 7.8, 2 mM β-ME and 5.6% glycerol. Phospholipid (50 mg/ml in 0.5% CHAPS) is added directly to the sample, which is in 1% CHAPS, then diluted by a cocktail containing the remaining assay components. Reconstitution of activity is presumed to be based on the incorporation of wax synthase into the phospholipid vesicles. Wax synthase is sensitive to detergent and requires the amount of phospholipid (PL) and detergent (CHAPS) to be balanced at 2.8/1 (CHAPS/PL, w/w) in the assay for maximal activity. Assays for wax synthase activity in samples concentrated by ultra-filtration require a readjustment of the sample volume assayed because of the concentration of CHAPS. Introducing too much CHAPS into the assay results in inhibition of activity. If samples are concentrated by ultrafiltration, the optimum volume of sample to be assayed may be reestablished by performing a concentration curve of %CHAPS in the assay using a small amount of sample and assaying at a fixed concentration of phospholipid and NaCl. Wax synthase is less sensitive to changes in PL concentration than it is to changes in CHAPS concentration.

D. Analysis of Assay Products

For analyzing the products of either the microsomal membrane preparation wax synthase assay or the solubilized wax synthase assay, two protocols have been developed. One protocol, described below as "extensive assay" is more time-consuming, but yields more highly quantitative results. The other protocols, described below as "quick assay" also provides a measure of wax synthase activity, but is faster, more convenient and less quantitative.

1. Extensive Analysis: Following addition of the sodium sulphate and vortexing the sample, the upper organic phase is removed and the lower aqueous phase is washed with 4 ml hexane/isopropanol (7:2 v/v). The organic phases are pooled and evaporated to dryness under nitrogen. The lipid residue is resuspended in a small volume of hexane, and an aliquot is assayed for radioactivity by liquid scintillation counting. The remainder of the sample can be used for TLC analysis of the labeled classes and thereby give a measure of total wax produced.

For lipid class analysis the sample is applied to a silica TLC plate, and the plate is developed in hexane/diethyl ether/acetic acid (80:20:1 or 70:30:2 v/v/v). The distribution of radioactivity between the lipid classes, largely wax esters, free fatty acids, fatty alcohols, and polar lipids at the origin, is measured using an AMBIS radioanalytic imaging system (AMBIS Systems Inc., San Diego, Calif.). If necessary the individual lipid classes can be recovered from the TLC plate for further analysis. Reversed-phase TLC systems using C18 plates developed in methanol have also been used for the analysis.

2. Quick Analysis: Following addition of the sodium sulfate and vortexing the sample, a known percentage of the organic phase is removed and counted via liquid scintillation counting. This calculation is used to estimate the total counts in the organic phase. Another portion of the organic phase is then removed, dryed down under nitrogen, redissolved in hexane and spotted on TLC plates and developed and scanned as described for the detailed assay. In this manner the percentage of the total counts which are incorporated into wax is determined.

Example 2

Further Studies to Characterize Wax Synthase Activity

A. Seed Development and Wax Synthase Activity Profiles

Embryo development was tracked over two summers on five plants in Davis, Calif. Embryo fresh and dry weights were found to increase at a fairly steady rate from about day 80 to about day 130. Lipid extractions reveal that when the embryo fresh weight reaches about 300 mg (about day 80), the ratio of lipid weight to dry weight reaches the maximum level of 50%.

Wax synthase activity was measured in developing embryos as described in Example 1B. As the jojoba seed coats were determined to be the source of an inhibiting factor(s), the seed coats were removed prior to freezing the embryos in liquid nitrogen for storage at −70° C.

Development profiles for wax synthase activities as measured in either a cell free homogenate or a membrane fraction, indicate a large induction in activity which peaks at approximately 110–115 days after anthesis. Embryos for enzymology studies were thus harvested between about 90 to 110 days postanthesis, a period when the wax synthase activity is high, lipid deposition has not reached maximum levels, and the seed coat is easily removed. The highest rate of increase of wax synthase activity is seen between days 80 and 90 postanthesis. Embryos for cDNA library construction were thus harvested between about 80 to 90 days postanthesis when presumably the rate of synthase of wax synthase protein would by maximal. Correspondingly, the level of mRNA encoding wax synthase would be presumed to be maximal at this stage.

B. Microsomal Membrane Preparation

Jojoba embryos are harvested at approximately 90–110 days after flowering, as estimated by measuring water content of the embryos (45–70%). The outer shells and seed coats are removed and the cotyledons quickly frozen in liquid nitrogen and stored at −70° C. for future use. For initial protein preparation, frozen embryos are powdered by pounding in a steel mortar and pestle at liquid nitrogen temperature. In a typical experiment, 70 g of embryos are processed.

The powder is added, at a ratio of 280 ml of solution per 70 g of embryos, to the following high salt solution: 3M NaCl, 0.3M sucrose, 100 mM HEPES, 2 mM DTT, and the protease inhibitors, 1 mM EDTA, 0.7 mg/ml leupeptin, 0.5 mg/ml pepstatin and 17 mg/ml PMSF. A cell free homogenate (CFH) is formed by dispersing the powdered embryos in the buffer with a tissue homogenizer (Kinematica, Switzerland; model PT10/35) for approximately 30 sec. and then filtering through three layers of Miracloth (CalBioChem, LaJolla, Calif.). The filtrate is centrifuged at 100,000×g for one hour.

The resulting sample consists of a pellet, supernatant and a floating fat pad. The fat pad is removed and the supernatant fraction is collected and dialyzed overnight (with three changes of the buffering solution) versus a solution containing 1M NaCl, 100 mM HEPES, 2 mM DTT and 0.5M EDTA. The dialyzate is centrifuged at 200,000×g for 1½ hour to yield a pellet, DP2. The pellet is suspended in 25 mM HEPES and 10% glycerol, at 1/20 of the original CFH volume, to yield the microsomal membrane preparation.

Activity is assayed as described in Example 1. Recovery of wax synthase activity is estimated at 34% of the original activity in the cell free homogenate. Wax synthase activity in this preparation is stable when stored at −70° C.

C. Substrate Specificity

Acyl-CoA and alcohol substrates having varying carbon chain lengths and degrees of unsaturation were added to microsomal membrane fractions prepared as described above to determine the range of substrates recognized by the jojoba wax synthase. Tax synthase activity was measured as described in Example 1B, with acyl specificity measured using 80 mM of acyl-CoA substrate and 100 mM of radiolabeled oleyl alcohol. Alcohol specificity was measured using 100 mM of alcohol substrate and 40 mM of radiolabeled eicosenoyl-CoA. Results of these experiments are presented in Table 1 below.

TABLE 1

Acyl and Alcohol Substrate Specificity of
Jojoba Wax Synthase

| Substrate Structure | Wax synthase Activity (pmoles/min) | |
|---|---|---|
| | Acyl Group | Alcohol Group |
| 12:0 | 12 | 100 |
| 14:0 | 95 | 145 |
| 16:0 | 81 | 107 |
| 18:0 | 51 | 56 |
| 20:0 | 49 | 21 |
| 22:0 | 46 | 17 |
| 18:1 | 22 | 110 |
| 18:2 | 7 | 123 |
| 20:1 | 122 | 72 |
| 22:1 | 39 | 41 |
| 24:1 | 35 | 24 |

The above results demonstrate that the jojoba wax synthase utilizes a broad range of fatty acyl-CoA and fatty alcohol substrates.

In addition, wax synthase activity towards various acyl-thioester substrates was similarly tested using palmitoyl-CoA, palmitoyl-ACP and N-acetyl-S-palmitoyl cysteamine as acyl substrates. The greatest activity was observed with the acyl-CoA substrate. Significant activity (~10% of that with acyl-CoA) was observed with acyl-ACP, but no activity was detectable with the N-acetyl-S-palmitoyl cysteamine substrate.

D. Effectors of Activity

Various sulphydryl agents were screened for their effect on wax synthase activity. Organomercurial compounds were shown to strongly inhibit activity. Iodoacetamide and N-ethylmaleamide were much less effective. Inhibition by para-hydroxymercuribenzoate was observed, but this inhibition could be reversed by subsequent addition of DTT. These results demonstrate that inhibition by para-hydroxymercuribenzoate involves blocking of an essential sulphydryl group.

Example 3

Purification of Jojoba Wax Synthase

Methods are described which may be used for isolation of a jojoba membrane preparation having wax synthase activity, solubilization of wax synthase activity, and further purification of the wax synthase protein.

A. Microsomal Membrane Preparation

The following modification of the method described in Example 2 is employed and provides an improved membrane fraction useful for purification of wax synthase from solubilized membranes.

Typically, 100 g of jojoba embryos are added to 400 ml of extraction buffer (40 mM Tricine-NaOH, pH 7.8, 200 mM KCl, 10 mM EDTA, 5 mM β-mercaptoethanol), ground in a blender, and homogenized with a Polytron tissue disrupter. All subsequent steps are performed at 4° C. The blended material is filtered through Miracloth (CalBioChem). Centrifugation (20,000×g; 20 min.) of the filtrate yielded a floating wax layer, a turbid supernatant fraction and a dark green pellet. The supernatant fraction is collected and centrifuged (100,000×g, 2 h) to obtain membrane pellets which are then resuspended in 40 ml of Buffer A (25 mM Tricine-NaOH, pH 7.8, 200 mM KCl, 5 mM EDTA, 5 mM β-mercaptoethanol) containing 50% (w/v) sucrose. This homogenate is distributed into four SW28 centrifuge tubes (Beckman) and each is overlaid with 10 ml Buffer A containing 20% sucrose and then with 13 ml Buffer A. After centrifugation (28,000 rpm; 2 h), a membrane fraction is collected from the 20%/50% sucrose interface, diluted with four volumes Buffer A and collected by centrifugation (200,000×g; 1 h). The membranes are then homogenized in 10 ml storage buffer [25 mM Tricine-NaOH, pH 7.8, 1 M NaCl, 10% (w/v) glycerol, 5 mM β-mercaptoethanol)]. The protein concentration of membranes prepared via the protocol is typically between 7 and 9 mg/ml. Protein concentrations are estimated as described (Bradford, 1976) using BSA as the protein standard.

B. Solubilization of Wax synthase Protein

The membrane suspension is adjusted to approximately 0.83 mg of protein per ml by dilution with storage buffer (25 mM Tricine-NaOH, pH 7.8, 1M NaCl, 10% glycerol, 5 mM β-mercaptoethanol). Solid 3-([3-cholamidopropyl] dimethylammonio)-1-propanesulfate (CHAPS) is added to achieve a final concentration of 2% (w/v) and a detergent to protein ratio of 24:1. After incubation on ice for 1 hr, the sample is centrifuged (200,000 g for 1 hr), and the supernatant fraction collected.

C. Purification of Wax Synthase Activity

The 200,000 g supernatant fraction is diluted (with 0.57% CHAPS, 25 mM Tricine-NaOH, pH 7.8, 20% glycerol) to yield final concentrations of NaCl and CHAPS of 0.3M and 1%, respectively. The sample is loaded onto a Blue A agarose (Amicon, Inc., Beverly, Mass.) column that has been equilibrated with buffer B (25 mM Tricine-NaOH, pH 7.8, 1% CHAPS, 20% glycerol,) containing 0.3M NaCl. After washing with equilibration buffer, wax synthase activity is eluted with buffer B containing 2M NaCl. Active fractions eluted from the Blue A column are pooled (Blue Pool) and used for further chromatography.

Two purification protocols were used for band identification and further purification of the wax synthase protein. In Protocol 1 (FIG. 1), the Blue Pool was concentrated 5.4 fold by ultrafiltration in a pressure cell fitted with a YM 30 membrane (Amicon Inc., Beverly, Mass.). One-half of the concentrate was applied to a Ceramic Hydroxyapatite (CHT) column (Bio-Scale CHT-2; Bio-Rad, Hercules, Calif.) equilibrated in buffer B containing 2M NaCl. The column was washed with 6 column volumes of equilibration buffer and bound proteins were eluted with buffer B containing 0.1M dipotassium phosphate and 2M NaCl. After reequilibration of the CHT column, the second half of the Blue Pool concentrate was chromatographed in the same manner. In order to detect activity, wax synthase was assayed according to the protocol for samples concentrated by ultrafiltration. Wax synthase activity, measured on CHT-Run 1, was found in the flow through and wash. Protein profiles of the two CHT runs were identical so the CHT-run 2 was not assayed. Active fractions from the two CHT runs were pooled and concentrated 10 fold and applied to a Sephacryl S100 HR column (2.5×90 cm) equilibrated in buffer B with 1.0 M NaCl. Protein and activity determinations were made and active fractions were selected from the retained portion of the run which maximized activity and minimized protein. The S100 pool (fractions 64–70) was applied to a crystalline hydroxylapatite (HA) column (Bio-Gel HT; Bio-Rad, Hercules, Calif., 1×19.3 cm) equilibrated in buffer B with 1 M NaCl. Again, the majority of the wax synthase activity was present in the flow through and wash. Bound proteins were eluted in buffer B with 0.1M dipotassium phosphate, and 1M NaCl. Fractions from the final HA run were examined by SDS-PAGE. A single protein migrating at 33 kD on SDS-PAGE was correlated with the presence of wax synthase activity.

Figure 2A:
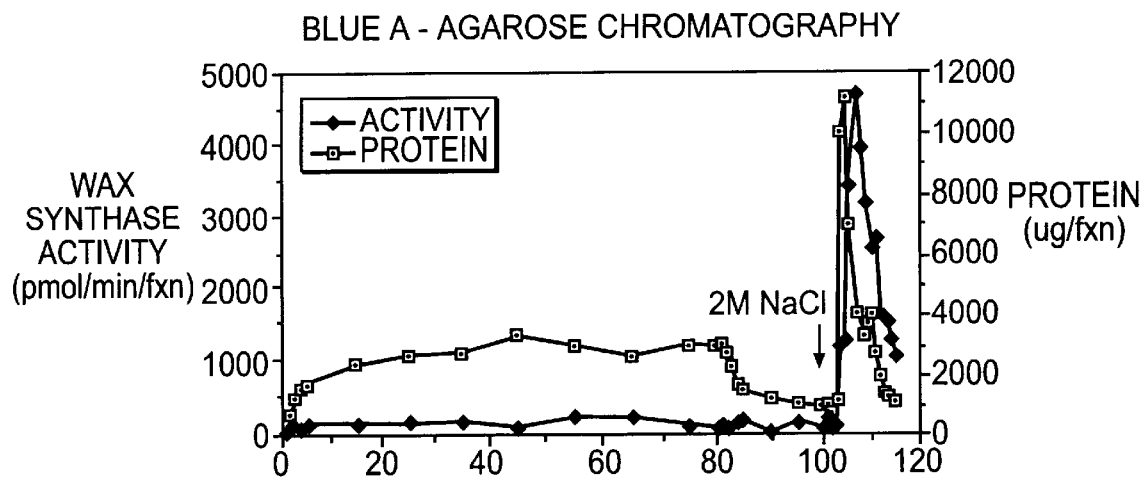
FIG. 2A provides results of Blue A agarose chromatography.
Figure 2B:
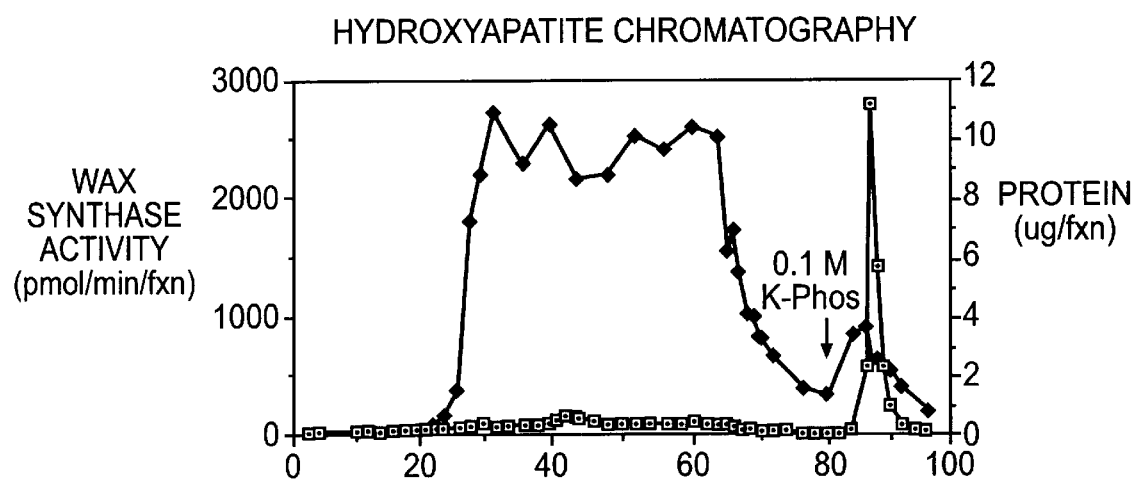
FIG. 2B provides results of hydroxyapatite chromatography.
Figure 2C:
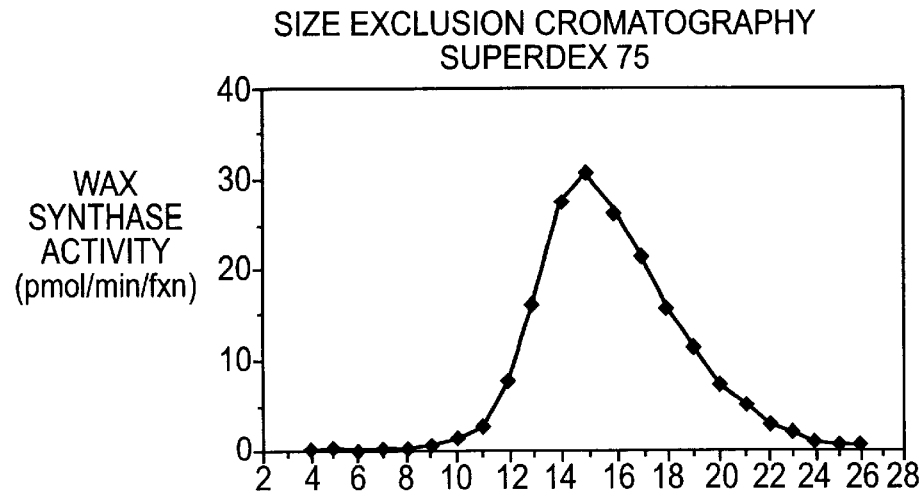
FIG. 2C provides results of Superdex 75 size exclusion chromatography.

In a second preparation (Protocol 2, FIG. 2) the Blue Pool was applied directly to a crystalline HA column (1×11.7 cm), equilibrated in buffer B with 1M NaCl, without concentration. Two fractions were selected for further purification by size exclusion chromatography on a Superdex 75 HR 10/30 column (Bio-Rad, Hercules, Calif.; sizing range: 5000–75,000 daltons) equilibrated with 25 mM Tricine-NaOH, pH 7.8, 1% CHAPS, 20% glycerol, 1M NaCl. Wax synthase activity was measured according to the protocol described for solubilized samples in Example 1C. One fraction eluted early in the flow through of the HA column (fraction 31) and the other eluted in the wash (fraction 67). The protein profiles of the two fractions were different based on SDS-PAGE analysis. Both Superdex 75 runs were examined by gradient SDS-PAGE and a protein of approximately 33 kD was identified that chromatographed with activity. A calibration curve was generated using molecular mass standards chromatographed under the same buffer and column conditions. Comparison of the elution volume of the peak of Wax Synthase activity to this standard curve yielded a value of 48 kDa for the molecular mass of the solubilized enzyme.

A chart representing the purification of wax synthase from Protocol 1 (Table 2) shows a 150 fold purification of the enzyme from the solubilized protein fraction.

TABLE 2

Purification of Jojoba Wax Synthase

| Purification Step | Enzyme Activity (nmol/min) | Yield % | Protein (mg) | Specific Activity (nmol/min/mg) | Purification (fold) |
|---|---|---|---|---|---|
| Solubilized Fraction | 274.4 | 100 | 415 | 0.7 | 1 |
| Blue A Agarose | 214.7 | 78.2 | 15 | 14.3 | 22 |
| Ceramic Hydroxyapatite | 176.6 | 64.3 | 6.4 | 27.6 | 42 |
| Sephacryl S-100 (sizing) | 41.3 | 15.1 | 1.2 | 33.1 | 50 |
| Hydroxyapatite (crystalline) | 18.8 | 6.9 | 0.2 | 99.2 | 150 |

D. SDS PAGE Analysis

Samples from the column fractions were diluted in SDS PAGE sample buffer (1×buffer=2% SDS, 250 mM β-mercaptoethanol, 0.0025% bromphenol blue) and analyzed by electrophoresis. Polyacrylamide gradient gel electrophoresis (10–13%) was carried out according to the method of Laemmli (*Nature* (1970) 227:680–685) with some of the modifications of Delepelaire (*Proc. Nat. Acad. Sci.* (1979) 76:111–115). Sodium dodecyl sulfate was used in the upper reservoir buffer at 0.1% but was ommitted from the lower reservoir buffer, stacking and resolving gels. The stacking gel contained 5% of a 30% acrylamide stock (29.2% acrylamide, 0.8% N,N'-bis-methyleneacrylamide, w/v), 0.06% ammonium persulfate (w/v) and 0.1% TEMED (v/v). The resolving gel contained a 10–13% linear gradient of acrylamide stock stabilized by a 0–10% linear gradient of sucrose. Electrophoresis was carried out at room temperature at 150V, constant voltage, for 9–10 hours. Proteins were visualized by staining with silver according to the method of Blume et al. (*Electrophorsis* (1987) 8:93–99 or with Coomassie Blue (0.1% Coomassie Blue R-250, 50% methanol, 10% acetic acid). The 33 kDa protein identified as wax synthase does not appear as a major component of the active fraction until purification through the hydroxyapatite column. Following purification Protocol 1 (Example 3C) the only protein that correlates with activity on the final column is one at 33 kDa.

Example 4

Preparation of Protein for In-Gel Digestion

A. Preparation of Samples for SDS-PAGE by Concentration

Odd numbered fractions from the flow through/wash of the final HA column (Protocol 1) were pooled and concentrated three fold by ultrafiltration in a pressure cell fitted with a YM 30 membrane (Amicon, Inc., Beverly, Mass.). The sample was further concentrated using two Centricon-30 units (Amicon, Inc., Beverly, Mass.) to volumes of approximately 50 µ. Each sample was treated with 6 µl SDS Cocktail (4 µl 20% SDS, 1 µl 14.3M β-mercaptoethanol, and 1 µl 0.1% Bromophenol Blue). After sitting at room temperature for 15 minutes, the samples were applied to a 10–13% acrylamide gradient gel (Example 3D) (16×16 cm×1 mm thick) and proteins were resolved by electrophoresis at 150V, constant voltage, for 9.5 hours. The gel was stained with 0.1% Coomassie Blue in 50% methanol, 10% acetic acid for 15 minutes then destained in 50% methanol, 10% acetic acid for 2×20 minutes, The 33 kDa Wax Synthase band was excised from the gel and destained in 50% ethanol for 3×20 minutes. One lane contained a streak of protein and was not used in the final digestion.

B. Preparation of Samples for SDS-PAGE by Precipitation

Aliquots (0.8 ml) of the even numbered fractions from the final HA column (Protocol 1) were pooled in groups of three over the column profile. The pools were divided equally into three, 1.5 ml vials. Protein was precipitated by the addition of 0.2 ml 40% TCA. After 30 minutes on ice the samples were centrifuged (12,000×g, 15 minutes at 4 C) to pellet the precipitated protein. The supernatants were removed and the pellets washed twice with 0.6 ml ice cold acetone. The final three pellets for each pooled set of samples were resuspended with the same 50 µl of SDS sample buffer by transfering the buffer from one vial to the next. The emptied vials, that had already been resuspended, were washed with 10 µl of sample buffer for a total resuspended volume of 60 µl for each pooled sample. The samples were applied to a 12% acrylamide Tris/Glycine mini-gel (Novex, San Diego, Calif., 1.5 mm×10 well) and proteins were resolved by electrophoresis at 150 V, constant voltage, for 20 minutes beyond the elution of dye from the foot of the gel. The gel was stained with Coomassie Blue and destained using Gel-Clear (Novex, San Diego, Calif.). Wax Synthase was excised from three non-equivalent lanes on the gel representing the peak and tailing fractions from the column. The gel slices were placed in 1.5 ml vials and destained with 1 ml of 50% methanol, 10% acetic acid for 2 hours. The destain solution was removed and the gel slices were frozen in liquid nitrogen and sent on dry ice, overnight, to the W M Keck Foundation Biotechnology Resource Laboratory at Yale University for in-gel-digestion. One gel slice from the sample concentrated by ultrafiltration and three gel slices from the samples concentrated by precipitation were pooled for in-gel tryptic digestion.

Example 5

Determination of Amino Acid Sequence

Protein sequencing was performed at the W.M. Keck Foundation Biotechnology Resource Laboratory, Yale University. Procedures include amino acid analysis of a portion (10–15%) of the gel slice for quantitation and amino acid composition, digestion of the protein with one of the proteolytic enzymes (trypsin or lysyl endopeptidase), and fractionation of the products by reverse phase HPLC. Absorbance peaks are selected from the HPLC run and subjected to laser desorption mass spectrometry to determine the presence, amount, and mass of the peptide prior to protein sequencing. The longest peptides are selected for microsequencing.

Amino acid sequences of jojoba wax synthase peptides obtained by trypsin digestion are presented in Table 3 below using the one letter code.

TABLE 3

Amino Acid Sequence of Jojoba Wax Synthase Tryptic Peptides

| | | |
|---|---|---|
| WSpep29 | SEQ. ID NO. 3 | FVPAVAPHGGALR |
| WSpep33 | SEQ. ID NO 4 | TIDEYPVMFNYTQK |

Example 6

Purification of Additional Wax Syntheases and Reductases

A. Adaptation of jojoba wax synthase solubilization and purification methods to obtain partially purified preparations of wax synthase from other organisms are described.

Acinetobacter

Cells of *Acinetobacter calcoaceticus* strain BD413 (ATCC #33305) are grown on ECLB (*E. coli* luria broth), collected during the logarithmic growth phase and washed in a buffer containing either HEPES-NaOH, pH 7.5, or Tricine-NaOH pH 7.8, in 0.1M NaCl, 1 mM DTT and protease inhibitors. Washed cells were resuspended in fresh buffer and ruptured by passage through a French pressure cell (two passes at ~16,000 p.s.i.). Unbroken cells are removed by centrifugation at 5000×g for 10 minutes, and membranes are collected by centrifugation at 100,000×g for 1 hour. The membrane pellet is homogenized in storage buffer (25 mM HEPES-NaOH, pH 7.5, or 25 mM Tricine-NaOH, pH 7.8, in 10% (w/v) glycerol, 100 mM NaCl). Wax synthase activity is detected in these membranes using assay conditions described for the jojoba enzyme in Example 1B, using [$1-^{14}$] palmitoyl-CoA and 18:1 alcohol as the substrates.

Wax synthase activity is solubilized by incubation of the membranes with 2% CHAPS in the presence of 0.5M NaCl, at a detergent to protein ratio of 5:1. Solubilization of the activity is demonstrated by the detection of wax synthase enzyme activity in the supernatant fraction after centrifugation at 200,000 g for 1 hour and by size exclusion chromatography (i.e. the activity elutes from the column in the retained fractions as a symmetrical peak). The activity of the solubilized enzyme is detected by simple dilution of the CHAPS concentration to ~0.3% (i.e. to below its CMC). Incorporation of the enzyme into phospholipid vesicles is not required to detect solubilized activity.

For purification, the solubilized Acinetobacter wax synthase activity is subjected to chromatographic procedures similar to those described for the jojoba wax synthase. In one protocol, the soluble protein preparation is loaded to a Blue A agarose column under low salt conditions (100 mM NaCl in a column buffer containing 0.75% % CHAPS, 10% glycerol, 25 mM HEPES-NaOH, pH 7.5) and eluted from the column using 1.0M NaCl in the column buffer.

Size exclusion chromatography on Superose 12 (Pharmacia; Piscataway, N.J.) medium is used to obtain an estimate of the size of the native enzyme. Comparison to molecular mass standards chromatographed under identical conditions yields an apparent mass of ~40 kDa for the solubilized wax synthase.

In another protocol, solubilized protein is loaded onto a Blue A column equilibrated with 25 mM Tricine-NaOH, pH 7.8, 1% CHAPS, 20% glycerol containing 0.1M NaCl and eluted in the same buffer containing 1.0M NaCl. The eluted material is then loaded onto a hydroxyapatite column equilibrated with column buffer containing 1.0 M NaCl and unlike the jojoba wax synthase, the acinetobacter wax synthase activity binds the column and is eluted in a gradient of 1–100 mM dipotassium phosphate. When examined by SDS-PAGE, several protein candidates can be correlated with wax synthase activity.

Euglena

*Euglena gracilis*, strain Z (ATCC No. 12716) is grown heterotrophically in the dark (Tani et al. (1987) *Agric. Biol. Chem.* 51:225–230) at ~26° C. with moderate shaking. Cells are collected and washed in buffer containing 25 mM Bis-Tris-Propane, pH 7.0, 0.25M NaCl and 1 mM EDTA. Washed cells are resuspended in fresh buffer and ruptured by passage through a French pressure cell (two passes at ~16,000 p.s.i.). Unbroken cells, cell debris and nuclei are removed by centrifugation at 20,000×g for 20 minutes, and microsomal membranes are collected by centrifugation at 200,000×g for 1 hour. The membrane pellet is homogenized in storage buffer (25 mM Bis-Tris-Propane, pH 7.0, 0.25M NaCl, 10% (w/v) glycerol and 1 mM EDTA). Wax synthase activity is detected in these membranes using assay conditions as described for the jojoba enzyme. The radiolabelled substrate is the same as for the jojoba example (i.e. [$1-^{14}$] palmitoyl-CoA), however, 16:0 rather than 18:1 is used as the alcohol acceptor, and Bis-Tris-Propane buffer at pH 7.0 is utilized.

The Euglena wax synthase activity is solubilized by incubation of the membranes with 2% CHAPS in the presence of 0.5M NaCl. Solubilization of the protein is demonstrated by the detection of enzyme activity in the supernatant fraction after centrifugation at 200,000×g for 1 hour. The activity of the solubilized enzyme is detected by dilution of the CHAPS concentration to ~0.3% (i.e. to below its CMC). It is not necessary to incorporate the enzyme into phospholipid vesicles as was the case for the solubilized jojoba wax synthase.

For partial purification, the solubilized Euglena wax synthase activity is subjected to chromatographic separation on Blue A agarose medium. The column is equilibrated with 0.1M NaCl in a column buffer containing; 25 mM Bis-Tris-Propane, pH 7.0, 20% (w/v) glycerol, 0.75% CHAPS and 1 mM EDTA. The sample containing solubilized wax synthase activity is diluted to 0.1M NaCl and loaded onto a 1×7 cm column (5.5 ml bed volume). The column is washed with equilibration buffer and subjected to a linear NaCl gradient (0.1M to 1.0M NaCl) in column buffer. Wax synthase activity is eluted as a broad peak in the last half of the salt gradient.

SDS-PAGE analysis of column fractions reveals that the polypeptide complexity of the activity eluted from the column is greatly reduced relative to the loaded material. A polypeptide with an apparent molecular mass of ~41 kD was observed to track with wax synthase activity in the column fractions. Further purification techniques, such as described for jojoba and Acinetobacter are conducted to verify the association of wax synthase activity with the ~41 kD peptide.

For further analysis of wax synthase activity in Euglena, size exclusion chromatography was conducted as follows. A microsomal membrane preparation was obtained from Euglena cells grown on liquid, heterotrophic, medium (Tani et al., supra) in the dark. Wax synthase activity was solubilized by treating the membranes with 2% (w/v) CHAPS and 500 mM NaCl in a buffered solution (25 mM Bis-Tris, pH 7.0, 1 mM EDTA and 10% (w/v) glycerol) for 1 hour on ice. After dilution of the CHAPS to 0.75% and the NaCl to 200 mM by addition of a dilution buffer, the sample was centrifuged at ~200,000×g for 1.5 hours. The supernatant fraction was loaded onto a Blue A dye column pre-equilibrated with Column Buffer (25 mM Bis-Tris pH 7.0, 1 mM EDTA, 10% glycerol, 0.75% CHAPS) which also contained 200 mM NaCl. The column was washed with Column Buffer containing 200 mM NaCl until the A280 of the effluent returned to the preload value. Wax synthase activity which had bound to the column was released by increasing the NaCl concentration in the Column Buffer to 1.5M. The fractions from the Blue A column containing wax synthase activity released by the 1.5M NaCl (~20 ml combined volume) were pooled and concentrated approximately 30-fold via ultrafiltration (Amicon pressure cell fitted with a YM 30 membrane). The concentrated material from the Blue A column was used as the sample for a separation via size exclusion chromatography on Superose 12 medium (Pharmacia).

Approximately 200 µl of the sample was loaded onto a Superose 12 column (HR 10/30), pre-equilibrated with Column Buffer containing 0.5M NaCl, and developed at a flow rate of 0.1 ml/min. The wax synthase activity eluted from the column as a smooth peak. Comparison of the elution volume of the wax synthase activity with the elution profiles of molecular mass standard proteins yielded an estimate of 166 kD for the apparent molecular mass of the enzyme. Fractions which contained wax synthase activity were analyzed via SDS-polyacrylamide gel electrophoresis followed by silver staining. A preliminary analysis of the polypeptide profiles of the various fractions did not reveal any proteins with molecular masses of 100 kD or greater whose staining intensity appeared to match the activity profile. The wax synthase polypeptide may be present as a minor component in the sample mixture that is not readily detectable on the silver-stained gel. Alternatively, the enzyme may be composed of subunits which are dissociated during SDS-PAGE.

B. In addition to jojoba reductase, such as that encoded by the sequence provided in FIG. 1, reductase proteins from other sources are also desirable for use in conjunction with the wax synthase proteins of this invention. Such proteins may be identified and obtained from organisms known to produce wax esters from alcohol and acyl substrates.

For example, an NADH-dependent fatty acyl-CoA reductase activity can be obtained from microsomal membranes isolated from *Euglena gracilis*. Methods which may be used to isolate microsomal membranes are described, for example in the published PCT patent application WO 92/14816 (application number PCT/US92/03164, filed Feb. 21, 1992). The reductase activity is solubilized from these membranes using the same approaches as used for jojoba reductase and wax synthase. Membranes are incubated on ice for one hour with various amounts of the detergents, CHAPS, in a buffering solution consisting of 25 mM BisTris, pH 6.9, 250 mM NaCl, 10% glycerol and 1 mM EDTA. The sample is then centrifuged at 200,000×g for one hour, and the supernatant and pellet fractions assayed for NADH-dependent reductase activity using radiolabeled palmitoyl-CoA and NADH as substrates. A convenient assay for reductase activity is described in PCT patent application WO 92/14816. Incubation of the membranes with 0.3, 0.5 or 0.7% (w/v) CHAPS results in retention of reductase activity in the supernatant fractions, indicative of solubilization of the enzyme. If CHAPS is omitted during the incubation and centrifugation, all of the reductase activity is found in the pellet fraction. All of the samples are diluted ten-fold in this same buffer solution prior to assaying in order to dilute the CHAPS present during the incubation. The presence of CHAPS in the assay at levels above the CMC (approximately 0.5% (w/v) results in inhibition of enzyme activity. Stability of the reductase activity in up to 2% CHAPS may be improved by increasing the glycerol concentration in the buffering solution to 20%. Reductase activity is recovered by dilution of the CHAPS to below the CMC.

Example 7

Isolation of Wax Synthase Nucleic Acid Sequences

DNA sequences encoding wax synthase peptides are obtained from jojoba using synthetic oligonucleotides designed from wax synthase peptide sequences. The wax synthase nucleic acid sequences may be obtained by amplification of DNA by polymerase chain reaction (PCR) using oligonucleotides as primers, or alternatively, by screening a cDNA or genomic DNA library by radiolabeling the oligonucleotides or previously isolated sequences for use as probes.

A. Construction of Jojoba cDNA Libraries

RNA is isolated from jojoba embryos collected at 80–90 days post-anthesis using a polyribosome isolation method, initially described by Jackson and Larkins (*Plant Physiol.* (1976) 57:5–10), as modified by Goldberg et al. (*Developmental Biol.* (1981) 83:201–217). In this procedure all steps, unless specifically stated, are carried out at 4° C. 10 gm of tissue are ground in liquid nitrogen in a Waring blender until the tissue becomes a fine powder. After the liquid nitrogen has evaporated, 170 ml of extraction buffer (200 mM Tris pH 9.0, 160 mM KCl, 25 mM EGTA, 70 mM MgCl2, 1% Triton X-100, 05% sodium deoxycholate, 1 mM spermidine, 10 mM β-mercaptoethanol, and 500 mM sucrose) is added and the tissue is homogenized for about 2 minutes. The homogenate is filtered through sterile miracloth and centrifuged at 12,000×g for 20 minutes. The supernatant is decanted into a 500 ml sterile flask, and 1/19 volume of a 20% detergent solution (20% Brij 35, 20% Tween 40, 20% Noidet p-40 w/v) is added at room temperature. The solution is stirred at 4° C. for 30 minutes at a moderate speed and the supernatant is then centrifuged at 12,000×g for 30 minutes.

About 30 ml of supernatant is aliquoted into sterile Ti 60 centrifuge tubes and underlaid with 7 ml of a solution containing 40 mM Tris pH 9.0, 5 mM EGTA, 200 mM KCl, 30 mM MgCl2, 1.8M sucrose, 5 mM β-mercaptoethanol. The tubes are filled to the top with extraction buffer, and spun at 60,000 rpm for 4 hours at 4° C. in a Ti60 rotor. Following centrifugation, the supernatant is aspirated off and 0.5 ml of resuspension buffer (40 mM Tris pH 9.0, 5 mM EGTA, 200 mM KCl, 30 mM $MgCl_2$, 5 mM β-mercaptoethanol) is added to each tube. The tubes are placed on ice for 10 minutes, after which the pellets are thoroughly resuspended and pooled. The supernatant is then centrifuged at 120×g for 10 minutes to remove insoluble material. One volume of self-digested 1 mg/ml proteinase K in 20 mM Tris pH 7.6, 200 mM EDTA, 2% N-laurylsarcosinate is added to the supernatant and the mixture incubated at room temperature for 30 minutes.

RNA is precipitated by adding 1/10 volume of sodium acetate and 2 volumes of ethanol. After several hours at 20° C. RNA is pelleted by centrifugation at 12,000× g at 4° C. for 30 minutes. The pellet is resuspended in 10 ml of TE buffer (10 mM Tris, 1 mM EDTA) and extracted with an equal volume of Tris pH 7.5 saturated phenol. The phases are separated by centrifuging at 10,000× g for 20 minutes at 4° C. The aqueous phase is removed and the organic phase is re-extracted with one volume of TE buffer. The aqueous phases are then pooled and extracted with one volume of chloroform. The phases are again separated by centrifugation and the aqueous phase ethanol precipitated as previously described, to yield the polyribosomal RNA.

Polysaccharide contaminants in the polyribosomal RNA preparation are removed by running the RNA over a cellulose column (Sigma-cell 50) in high salt buffer (0.5M NaCl, 20 mM Tris pH 7.5, 1 mM EDTA, 0.1% SDS). The contaminant binds to the column and the RNA is collected in the eluant. The eluant fractions are pooled and the RNA is ethanol precipitated. The precipitated total RNA is then resuspended in a smaller volume and applied to an oligo d(T) cellulose column to isolate the polyadenylated RNA.

Polyadenylated RNA is used to construct a cDNA library in the plasmid cloning vector pCGN1703, derived from the commercial cloning vector Bluescribe M13- (Stratagene Cloning Systems; San Diego, Calif.), and made as follows. The polylinker of Bluescribe M13- is altered by digestion with BamHI, treatment with mung bean endonuclease, and blunt-end ligation to create a BamHI-deleted plasmid, pCGN1700. pCGN1700 is digested with EcoRI and SstI (adjacent restriction sites) and annealed with a synthetic linker having restriction sites for BamHI, PstI, XbaI, ApaI and SmaI, a 5' overhang of AATT, and a 3' overhang of TCGA. The insertion of the linker into pCGN1700 eliminates the EcoRI site, recreates the SstI (also, sometimes referred to as "SacI" herein) site found in Bluescribe, and adds the new restriction sites contained on the linker. The resulting plasmid pCGN1702, is digested with HindIII and blunt-ended with Klenow enzyme; the linear DNA is partially digested with PvuII and ligated with T4 DNA wax synthase in dilute solution. A transformant having the lac promoter region deleted is selected (pCGN1703) and is used as the plasmid cloning vector.

Briefly, the cloning method for cDNA synthesis is as follows. The plasmid cloning vector is digested with SstI and homopolymer T-tails are generated on the resulting 3'-overhang stick-ends using terminal deoxynucleotidyl transferase. The tailed plasmid is separated from undigested or un-tailed plasmid by oligo(dA)-cellulose chromatography. The resultant vector serves as the primer for the synthesis of cDNA first strands covalently attached to either end of the vector plasmid. The cDNA-mRNA-vector complexes are treated with terminal transferase in the presence of deoxyguanosine triphosphate, generating G-tails at the ends of the cDNA strands. The extra cDNA-mRNA complex, adjacent to the BamHI site, is removed by BamHI digestion, leaving a cDNA-mRNA-vector complex with a BamHI stick-end at one end and a G-tail at the other. This complex is cyclized using an annealed synthetic cyclizing linker which has a 5' BamHI sticky-end, recognition sequences for restriction enzymes NotI, EcoRI and SstI, and a 3' C-tail end. Following ligation and repair the circular complexes are transformed into $E.\ coli$ strain DH5a (BRL, Gaithersburg, Md.) to generate the cDNA library. The jojoba embryo cDNA bank contains between approximately $1.5\times 10^6$ clones with an average cDNA insert size of approximately 500 base pairs.

Additionally, jojoba polyadenylated RNA is also used to construct a cDNA library in the cloning vector 1ZAPII/EcoRI (Stratagene, San Diego, Calif.). The library is constructed using protocols, DNA and bacterial strains as supplied by the manufacturer. Clones are packaged using Gigapack Gold packaging extracts (Stratagene), also according to manufacturer's recommendations. The cDNA library constructed in this manner contains approximately $1\times 10^6$ clones with an average cDNA insert size of approximately 400 base pairs.

B. Synthetic Oligonucleotides

In general, for use as PCR primers from single stranded DNA template reverse-transcribed from mRNA, oligonucleotides containing the sense orientation sequence corresponding to wax synthase peptide encoding sequences are prepared. These oligonucleotides are used as primers for the "forward" amplification reaction to produce sense strand DNA.

For the "reverse" reaction for amplification of the non-coding DNA strand, an oligonucleotide may be designed to be identical to a portion of a primer used to prepare DNA template for PCR. Alternatively, oligonucleotides which contain sequence complementary to wax synthase peptide encoding sequences may be used in combination with a "forward" wax synthase oligonucleotide primer as described above.

Where the wax synthase peptide sequences contain amino acids which may be encoded by a number of different codons, the forward or reverse primers may be "degenerate" oligonucleotides, i.e. containing a mixture of all or some of the possible encoding sequences for a particular peptide region. To reduce the number of different oligonucleotides present in such a mixture, it is preferable to select peptide regions which have the least number of possible encoding sequences when preparing the synthetic oligonucleotide for PCR primers. Similarly, where the synthetic oligonucleotide is to be used to directly screen a library for wax synthase sequences, lower degeneracy oligonucleotides are preferred.

Following is an example of the sequence SEQ. ID NO. 5 of peptide WSPEP33 (center line) and the forward (top line) and reverse (bottom line) DNA sequences that encode the peptide WSPEP33.

```
5'   TTY GTN CCN GCN GTN GCN CCN CAY GGN GGN GCN YTN MGN   3'

F   V   P   A   V   A   P   H   G   G   A   L   R

3'   AAR CAN GGN CGN CAN CGN GGN GTR CCN CCN CGN RAN KCN   5'
```

Following is an example of the sequence SEQ. ID NO. 5 of peptide WSPEP29 (center line) and the forward (top line) and reverse (bottom line) DNA sequences that encode the peptide WSPEP29.

I=inosine
Y=cytosine or thymine
R=adenine or guanine
O=inosine or cytosine

```
5' ACN ATH GAY GAR TAY CCN GTN ATG TTY AAY TAY ACN CAR AAR 3'

T   I   D   E   Y   P   V   M   F   N   Y   T   Q   K

3' TGN TAD CTR CTY ATR GGN CAN TAC AAR TTR ATR TGN GTY TTY 5'
```

Following is an example of the sequence SEQ. ID NO. 7 of peptide WSPEP14 (center line) and the forward (top line) and reverse (bottom line) DNA sequences that encode the peptide WSPEP14.

```
5' TTY MGN GAY GAY CCN WSN AAY GAY CAY 3'

F   R   D   D   P   S   N   D   H

3' AAR KCN CTR CTR GGN WSN TTR CTR GTR 5'
```

Following are sequences of synthetic oligonucleotides which may be used to obtain wax synthase sequences. The oligonucleotide names reflect the particular wax synthase peptide fragment numbers as listed in Example 5. The letter "F" in the oligonucleotide name designates a PCR forward reaction primer. The letter "R" designates a PCR reverse reaction primer.

WSPEP29-F1 SEQ. ID NO. 8 5' TTYGTNCCNGCNGT-NGC 3'

WSPEP29-F2 SEQ. ID NO. 9 5' GCNCCNCAYGGNG-GNGC 3'

WSPEP29-R1 SEQ. ID NO. 10 5' GCNCCNCCRTGNG-GNGC 3'

WSPEP29-R2 SEQ. ID NO. 11 5' GCNACNGCNG-GNACRAA 3'

WSPEP33-F1 SEQ. ID NO. 12 5' ACNATHGAYGAR-TAYCCNGT 3'

WSPEP33-F2 SEQ. ID NO. 13 5' CCNGTNATGT-TYAAYTAYAC 3'

WSPEP33-R1 SEQ. ID NO. 14 5' TTYTGNGTRTART-TRAACAT 3'

WSPEP33-R2 SEQ. ID NO. 15 5' AACATNACNGGR-TAYTCRTC 3'

WSPEP14-F1 SEQ. ID NO. 16 5' GAYGAYCCNWS-NAAYGAYCA

WSPEP14-R1 SEQ. ID NO. 17 5' TGRTCRTTNSWNG-GRTCRTC

The nucleotide base codes for the above oligonucleotides are as follows:

A=adenine
C=cytosine
G=guanine
H=adenine, cytosine or thymine
N=adenine, cytosine, guanine or thymine
W=adenine or thymine
S=guanine or cytosine
B=guanine, cytosine or thymine
K=guanine or thymine
M=adenine or cytosine
T=thymine
U=uracil C. PCR Reactions Poly(A)+RNA is isolated from total RNA prepared from jojoba tissue as described above. cDNA is prepared from poly(A)+ or total RNA by reverse transcription using the Marathon cDNA Amplification Kit (Clontech Laboraties Inc according to the manufacturer's directions. The jojoba cDNA is used in PCR reactions 1–16 set forth below.

PCR is conducted in a Perkin Elmer Cetus GeneAmp PCR System 9600 PCR machine using reverse transcribed single-stranded cDNA as template. Commercially available PCR reaction and optimization reagents are used according to manufacturer's specifications

| Reaction | Forward Primer | Reverse Primer |
| --- | --- | --- |
| 1 | WSPEP14-F1 | WSPEP29-R1 |
| 2 | WSPEP14-F1 | WSPEP29-R2 |
| 3 | WSPEP14-F1 | WSPEP33-R1 |
| 4 | WSPEP14-F1 | WSPEP33-R2 |
| 5 | WSPEP29-F1 | WSPEP14-R1 |
| 6 | WSPEP29-F1 | WSPEP33-R1 |
| 7 | WSPEP29-F1 | WSPEP33-R2 |
| 8 | WSPEP29-F2 | WSPEP14-R1 |
| 9 | WSPEP29-F2 | WSPEP33-R1 |
| 10 | WSPEP29-F2 | WSPEP33-R2 |
| 11 | WSPEP33-F1 | WSPEP14-R1 |
| 12 | WSPEP33-F1 | WSPEP29-R1 |
| 13 | WSPEP33-F1 | WSPEP29-R2 |
| 14 | WSPEP33-F2 | WSPEP14-R1 |
| 15 | WSPEP33-F2 | WSPEP29-R1 |
| 16 | WSPEP33-F2 | WSPEP29-R2 |

The temperature program used for PCR amplification is as follows: 1 cycle of 95 degrees C. for 2 minutes; 4 cycles of 95 degrees C. for 30 seconds, 60 degrees C. for 1 minute, and 72 degrees C. for 4 minutes; 4 cycles of 95 degrees C. for 30 seconds, 57 degrees C. for 1 minute, and 72 degrees C. for 4 minutes; 4 cycles of 95 degrees C. for 30 seconds, 54 degrees C. for 1 minute, and 72 degrees C. for 4 minutes; 4 cycles of 95 degrees C. for 30 seconds, 51 degrees C. for 1 minute, and 72 degrees C. for 4 minutes; and 25 cycles of 95 degrees C. for 30 seconds, 48 degrees C. for 1 minute, and 72 degrees C. for 4 minutes.

From reactions 3 and 4, a PCR product approximately 700 nucleotides in length was detected. The PCR product was purified using gel electrophoresis and cloned into pCR2.1 using a Topo TA cloning kit (Invitrogen Corp.). The DNA sequence of the cloned PCR product was determined and was 708 nucleotides long (FIG. 3).

The entire cDNA can be amplified using 5' and 3' RACE (Frohman et al., 1988) using the Marathon cDNA Amplification Kit (Clontech Laboraties Inc.) according to the manufacturers instructions. From the sequence of the 708 nucleotide PCR fragment derived using primers WSPEP14-F1 and WSPEP33-R2 the following primers were synthesized:

WSRACEF1 SEQ. ID NO. 18 GATTTGCCT-CATTTTGTGATCTCGGTGCT

WSRACEF2 SEQ. ID NO. 19 GACCTATACCCCCAGT-TCAACGAGCCATAC

WSRACEF3 SEQ. ID NO. 20 TTCAACGAGCCATACT-TAGCCACCTCGCTG

WSRACER1 SEQ. ID NO. 21 AACAACCACCCTC-CAGTCACCATCACGAAC

WSRACER2 SEQ. ID NO. 22 TTGCCTGAAACCGC-CTTCTTCACCACCATC

WSRACER3 SEQ. ID NO. 23 AAGATGTCTGACAC-CATGAGGTTCCACCTG

3'RACE reactions were set up using parimers WSRACEF1, WSRACEF2, and WSRACEF3. 5'RACE reactions were set up using parimers WSRACER1, WSRACER2, and WSRACER3. PCR reactions were performed according to the manufacturer's protocol (Clontech Laboratories Inc.). All 6 PCR reactions gave visible PCR products ranging in size from approximately 700 nucleotides to 1000 nucleotides. The PCR products were gel purified and cloned into pCR2.1 according to the manufacturer's protocol (Invitrogen Corp.). The DNA sequence of several clones from both the 5' and the 3'RACE reactions and the previous PCR product derived from primers WSPEP14-F1 and WSPEP33-R2 were assembled using Sequencher software (Gene Codes Corp.). The assembled sequence of all the PCR products contains the coding region of the cDNA sequence (SEQ ID NO: 2).

To isolate a gene fragment suitable for cloning the wax synthase gene into expression cassettes for plant lipid modification, the coding region of the gene (SEQ ID NO: 2) can be amplified from cDNA using the primers WAXSYN-FOR and WASXYNREV. The sequence SEQ ID NO.24 of WAXSYNFOR is GGATCCGTCGACACAATGGAGGT-GGAGAAGGAGCTAAAG, and the sequence SEQ ID NO.25 of WASXYNREV is GCATGCAGATCTCACCAC-CCCAACAAACCCATC. The PCR reaction is performed using the Marathon CDNA (Clontech Laboratories Inc.) according to the manufacturer's instructions. The PCR program consists of 30 cycles of 94 degrees C. for 15 seconds, 60 degrees C. for 1 minute, 72 degrees C. for 2 minutes.

Example 8

Generation of Transgenic Plants Containing the Wax Synthase cDNA

Two plant binary vectors were constructed. Plasmid pCGN8559 contains 3 genes necessary for wax biosynthesis: the condensing enzyme involved in fatty acid elongation to chain lengths greater than 18 carbons (KCS), the acyl-CoA reductase involved in formation of fatty alcohols, and the wax synthase. A control plasmid, pCGN8557, contains the KCS and acyl-CoA reductase genes. The Asp718 fragment of pCGN7698, which contains the jojoba acyl-CoA reductase under control of napin regulatory sequences, was cloned into the Asp718 site of binary vector pCGN5139 to form pCGN8555. The NotI fragment of pCGN7844, which contains the Lunaria KCS under control of napin regulatory sequences, was cloned into the NotI site of pCGN8555 to form pCGN8557. The SalI-BglII fragment from pCGN8538 which contains the coding region of the jojoba wax synthase gene (SEQ ID NO: 2), was cloned into the napin expression cassette of pCGN7770 digested with the same two restriction endonucleases to form pCGN8553. The Sse8387 fragment of pCGN8553, which contains the jojoba wax synthase under control of napin regulatory sequences, was cloned into the Sse8387 site of pCGN8557 to form pCGN8559. The binary vectors were introduced into *Agrobacterium tumefaciens* EHA105 via electroporation. The vectors were used to transform *Arabidopsis thaliana* ecotype No-O according to the vacuum infiltration protocol of Bent et al. (1994, Science 265:1856–1860).

Example 9

Analysis of the Seed Oil

Figure 4:
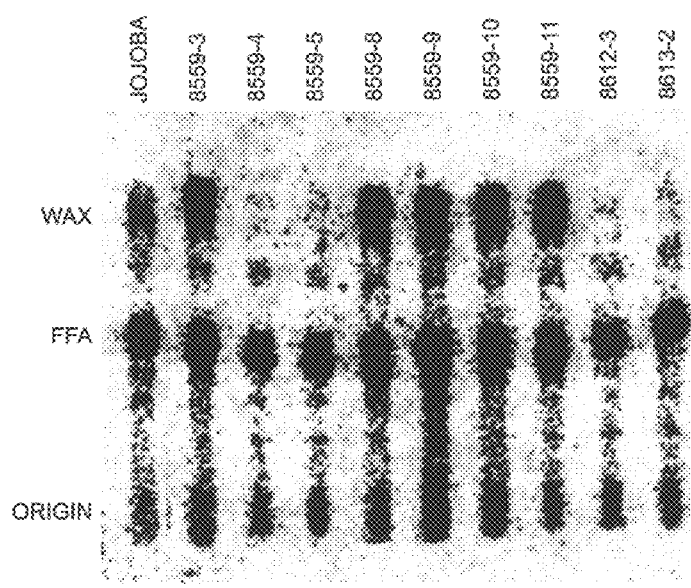
FIG. 4 provides the Radioimage of TLC plate showing incorporation of 1-$^{14}$C 16:0 CoA into wax in assays of the pellet fractions prepared from developing seeds of arabidopsis transformed with pCGN8559. A membrane fraction from developing jojoba seed is the positive control. Background activity is illustrated in the assays of arabidopsis plants 8612-3 and 8613-2.

Siliques were harvested from seven arabidopsis plants transformed with pCGN8559 which were in various stages of development. Developing seed was removed from ten siliques collected from each plant and homogenized in 275 µl of buffer (100 mM HEPES/NaOH pH 7.5, 250 mM NaCl). A portion of the homogenate (200 µl) was centrifuged at 16000× g for 20 minutes at 4° C. resulting in a supernatant and pellet. The pellet was resuspended in 200 µl of the same buffer. The homogenate and two fractions were assayed for wax synthase activity according to the protocol detailed in Example 1B. 25 µl of sample were used per assay in a final volume of 250 µl. The assay buffer contained 40 µM 1-$^{14}$C 16:0-CoA (specific activity 5 µCi/µmol), 200 µM 18:1 alcohol, 50 mM HEPES/NaOH pH 7.5, 250 mM NaCl and 2 mM β-mercaptoethanol. TLC analysis showed the incorporation of radiolabel from 1-$^{14}$C 16:0-CoA into a band which comigrated with a wax standard in 5 of the 7 plants analyzed (FIG. 4). This activity was detected in the homogenate and pellet fractions but not in the supernatant fraction. The wax synthase activity detected in these samples is several orders of magnitude greater than an endogenous wax synthase activity previously shown to be present in developing arabidopsis seed. The activity detected in 8612-3 and 8613-2 is indicative of this endogenous "background" activity. A positive control for wax activity was the jojoba (DP2) membrane fraction.

The above results demonstrate nucleic acid sequences obtained from partially purified wax synthase proteins are active in the formation of wax esters from fatty alcohol and fatty acyl substrates. Methods to obtain the wax synthase proteins and amino acid sequences thereof are provided. Such nucleic acid sequences may be manipulated to provide for transcription of the sequences and/or expression of wax synthase proteins in host cells, which proteins may be used for a variety of applications. Such applications include the production of wax ester compounds when the wax synthase is used in host cells having a source of fatty alcohol substrates, which substrates may be native to the host cells or supplied by use of recombinant constructs encoding a fatty acyl reductase protein which is active in the formation of alcohols from fatty acyl substrates.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity and understanding, it will be readily apparent to those of ordinary skill in the art in light of the teaching of this invention that certain changes and modifications may be made thereto without departing from the spirit or scope of the appended claims.

What is claimed is:

1. A recombinant DNA construct comprising a nucleic acid sequence which encodes a jojoba acyltransferase active in the formation of a wax ester, and a heterologous DNA sequence not naturally associated with said jojoba acyltransferase encoding sequence.

2. The construct of claim 1 wherein said wax ester is formed from a fatty alcohol and a fatty acyl-CoA substrate.

3. The construct of claim 1 wherein said jojoba acyltransferase is active toward a fatty acyl substrate having a carbon chain of the formula $C_{2X}$ wherein X is selected from the group 6–12.

4. The construct of claim 1 wherein said jojoba acyltransferase is active toward a fatty alcohol substrate having a carbon chain of the formula $C_{2X}$ wherein X is selected from the group 6–12.

5. The construct of claim 1 wherein said jojoba acyltransferase encoding sequence is from a seed plant.

6. The construct of claim 1 further comprising a promoter which provides for at least transcription of said jojoba acyltransferase encoding sequence in a host cell.

7. The construct of claim 6 wherein said promoter provides for expression of said jojoba acyltransferase encoding sequence in a plant cell.

8. The construct of claim 7 wherein said plant cell is a plant embryo seed cell.

9. The construct of claim 6 wherein said promoter provides for expression of said jojoba acyltransferase encoding sequence in a bacterial cell.

10. The construct of claim 7 wherein said promoter is from a gene preferentially expressed in a plant seed embryo cell.

11. A cell comprising a construct according to claim 1.

12. A plant cell comprising a construct according to claim 1.

13. A Brassica plant cell comprising a construct according to claim 1.

14. The construct of claim 1 wherein said jojoba acyltransferase comprises the peptide sequence TIDEYPVMFNYTQK (SEQ ID NO:4).

15. The construct of claim 6 wherein said promoter is a seed-specific promoter.

* * * * *